United States Patent
Barr et al.

(10) Patent No.: US 11,814,343 B2
(45) Date of Patent: Nov. 14, 2023

(54) CHROMIUM-CATALYZED PRODUCTION OF ALCOHOLS FROM HYDROCARBONS IN THE PRESENCE OF OXYGEN

(71) Applicant: Chevron Phillips Chemical Company LP, The Woodlands, TX (US)

(72) Inventors: Jared L. Barr, Bartlesville, OK (US); Carlos A. Cruz, Kingwood, TX (US); Masud M. Monwar, Bartlesville, OK (US); Max P. McDaniel, Bartlesville, OK (US); Kathy S. Clear, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 17/831,485

(22) Filed: Jun. 3, 2022

(65) Prior Publication Data

US 2022/0388932 A1 Dec. 8, 2022

Related U.S. Application Data

(60) Provisional application No. 63/208,045, filed on Jun. 8, 2021.

(51) Int. Cl.
*C07C 29/50* (2006.01)
*B01J 23/26* (2006.01)
*B01J 35/00* (2006.01)

(52) U.S. Cl.
CPC .............. *C07C 29/50* (2013.01); *B01J 23/26* (2013.01); *B01J 35/0053* (2013.01)

(58) Field of Classification Search
CPC ......... C07C 29/50; C07C 37/60; C07C 29/48; C07C 31/135; B01J 23/26; B01J 35/0053
See application file for complete search history.

(56) References Cited

U.S. PATENT DOCUMENTS

| | | |
|---|---|---|
| 3,201,476 A | 8/1965 | Baker |
| 3,857,901 A | 12/1974 | Dowden |
| 4,011,273 A | 3/1977 | Abend |
| 4,248,735 A | 2/1981 | McDaniel |
| 4,393,253 A | 7/1983 | Michaelson |
| 4,808,561 A | 2/1989 | Welborn, Jr. |
| 5,220,080 A | 6/1993 | Lyons |
| 5,300,154 A | 4/1994 | Ferber |
| 6,825,377 B1 | 11/2004 | Beller |
| 7,294,599 B2 | 11/2007 | Jensen |
| 7,304,199 B2 | 12/2007 | Xu |
| 7,407,591 B2 | 8/2008 | De Battisti |
| 7,601,665 B2 | 10/2009 | McDaniel |
| 7,649,062 B2 | 1/2010 | Matsunaga |
| 8,309,485 B2 | 11/2012 | Yang |
| 8,623,973 B1 | 1/2014 | McDaniel |
| 8,969,228 B2 | 3/2015 | Nazarpoor |
| 9,096,699 B2 | 8/2015 | McDaniel |
| 9,796,798 B2 | 10/2017 | Praetorius |
| 9,802,841 B2 | 10/2017 | Maruo |
| 9,988,468 B2 | 6/2018 | McDaniel |
| 10,213,766 B2 | 2/2019 | Praetorius |
| 10,287,369 B2 | 5/2019 | Schwerdtfeger |
| 10,654,953 B2 | 5/2020 | McDaniel |
| 11,180,435 B2 | 11/2021 | Cruz |
| 2008/0032886 A1 | 2/2008 | Yeh |
| 2014/0275457 A1* | 9/2014 | McDaniel ................ C08F 4/22 526/194 |
| 2017/0217866 A1 | 8/2017 | Boppana |
| 2019/0184389 A1 | 6/2019 | Neygandhi |
| 2019/0308172 A1 | 10/2019 | Zou |
| 2020/0086307 A1 | 3/2020 | Monwar |
| 2020/0087430 A1 | 3/2020 | Clear |
| 2021/0077981 A1 | 3/2021 | Cruz |
| 2021/0078926 A1 | 3/2021 | Barr |
| 2021/0078927 A1 | 3/2021 | McDaniel |

FOREIGN PATENT DOCUMENTS

| | | |
|---|---|---|
| CN | 101264953 B | 8/2010 |
| CN | 106893015 B | 9/2019 |
| CN | 108439533 B | 7/2020 |
| FR | 1045726 A | 12/1953 |
| JP | 2012101986 A | 5/2012 |
| WO | 2018125690 A1 | 7/2018 |
| WO | 2020060888 A2 | 3/2020 |

(Continued)

OTHER PUBLICATIONS

Awasthy, A.K. and Jan Rocek, "The Nature of the Transition State in the Oxidation of Olefins by Chromium (VI)," JACS 91;4, Feb. 12, 1969, pp. 991-996.
Baker, L. M., et al., Oxidation of olefins by supported chromium oxide, The Journal of Organic Chemistry, vol. 33, No. 2, pp. 616-618 (Year: 1968).
Barzan, et al., Ligands Make the Difference: Molecular Insights into CrVI/SiO2 Phillips Catalyst during Ethylene Polymerization, J. Am. Chem. Soc., 2017, 139, 47, 17064-17073.
Brown, et al., "Mechanism of Initiation in the Phillips Ethylene Polymerization Catalyst: Redox Processes Leading to the Active Site", ACS Catal. 2015, 5, 5574-5583.
Cainelli, et. al., "Reactivity and Structure Concepts in Organic Chemistry", vol. 19, "Chromium Oxidations in Organic Chemistry", Springer Verlag Berlin 1984, p. 8.

(Continued)

*Primary Examiner* — Jafar F Parsa
(74) *Attorney, Agent, or Firm* — Merchant & Gould P.C.

(57) ABSTRACT

Processes for converting a hydrocarbon reactant into an alcohol compound and/or a carbonyl compound are disclosed in which the hydrocarbon reactant and either a supported chromium (VI) catalyst or a supported chromium (II) catalyst are contacted, optionally with UV-visible light irradiation, followed by exposure to an oxidizing atmosphere and then hydrolysis to form a reaction product containing the alcohol compound and/or the carbonyl compound. The presence of oxygen significant increases the amount of alcohol/carbonyl product formed, as well as the formation of oxygenated dimers and trimers of certain hydrocarbon reactants.

20 Claims, No Drawings

(56) References Cited

FOREIGN PATENT DOCUMENTS

| | | |
|---|---|---|
| WO | 2020060889 A2 | 3/2020 |
| WO | 2021055270 A1 | 3/2021 |
| WO | 2021055271 A1 | 3/2021 |
| WO | 2021055272 A1 | 3/2021 |

OTHER PUBLICATIONS

Chakrabarti, et al., "Operando Molecular Spectroscopy During Ethylene Polymerization by Supported CrOx/SiO2 Catalysts: Active Sites, Reaction Intermediates, and Structure-Activity Relationship", Top. Catal. 2016, 59 p. 725-739.
Cruz, et al., "Identification of the Starting Group on the Initial PE Chain Produced by Phillips Catalyst", Macromolecules 2019, 52, 5750-5760.
Economy, et.al., "Supported Barium Chromate-A New Oxidation Catalyst", J. Catalysis, vol. 4, No. 4, Aug. 1, 1965, pp. 446-453.
Fendrick, et. al, "Actinacyclobutanes. Implementation of Thermochemically Based Strategies for the Ring-Opening Stoichiometric C-H Functionalization of Saturated and Olefinic Hydrocarbons", J. Am. Chem. Soc. 1986, 108, 425-437.
Finch, "Reduction Studies on Supported Chromic Anhydride Catalysts," Journal of Catalysis, 43, 1976, pp. 111-121.
Floryan, et al., 'Strain Effect and Dual Initiation Pathway in Cr(III)/SiO2 Polymerization Catalysts from Amorphous Periodic Models, J. Catalysis 2017, 346, 50-56.
Gierada, et al., "Active sites formation and their transformations during ethylene polymerization by the Phillips CrOx/SiO2 catalyst", J. Catal., 2017, 352, 314-328.
Groppo, et al., "The Structure of Active Centers and the Ethylene Polymerization Mechanism on the Cr/SiO2 Catalyst: A Frontier for the Characterization Method", Chem. Rev. 2005, 105, 115-183.
International Search Report and Written Opinion, PCT/US2020/050650, dated Dec. 2, 2020, 14 pages.
Joseph, et al., "Products of the Initial Reduction of the Phillips Catalyst by Olefins", Journal of Catalysis 377 (2019) 550-564.
Kissin, et al., "Chemistry of Olefin Polymerization Reactions with Chromium-Based Catalysts", Journal of Polymer Science: Part A: Polymer Chemistry, 2008, 46, 5330-5347.
Kohler, et al., "Infrared Spectroscopic Characterization of Chromium Carbonyl Species Formed by Ultraviolet Photoreduction of Silica-Supported Chromium(VI) in Carbon Monoxide," J. Phys. Chem. 1994, 98, pp. 4336-4342.
McDaniel, et. al., "The Activation Of The Phillips Polymerization Catalyst; I. Influence Of The Hydroxyl Population", J. Catalysis, vol. 82, No. 1, Jul. 1, 1983, pp. 98-109.
Milas, N .A., The hydroxylation of unsaturated substances. III. The use of vanadium pentoxide and chromium trioxide as Catalysts of hydroxylation, The Journal of the American Chemical Society, vol. 59, No. 11, pp. 2342-2344 (Year: 1937).
Milas, N.A. et al., The hydroxylation of unsaturated substances. IV. The catalytic hydroxylation of unsaturated hydrocarbons, The Journal of the American Chemical Society, vol. 59, No. 11, pp. 2345-2347 (Year: 1937).
Mino, et al., "Photoinduced Ethylene Polymerization on the CrVI/SiO2 Phillips Catalyst," J. Phys. Chem. C 2019, 123, 13 pp. 8145-8152.
Monwar, et.al., "Ethylene polymerization by hydrocarbon-reduced Cr/silica catalyst", Journal of Catalysis 394 (2021) 451-464.
Potter, et al., "Reduction of the Phillips Catalyst by Various Olefins: Stoichiometry, Thermochemistry, Reaction Products and Polymerization Activity", J. Catal. 344 (2016) 657-668.
Schwerdtfeger, E., et al., Reduction of Cr(VI) polymerization catalysts by non-olefinic hydrocarbons, Applied Catalysis A: General, 423-424, pp. 91-99 (Year: 2012).
Scott, et al. "Surface Organometallic Investigation of the Mechanism of Ethylene Polymerization by Silica-Supported Cr Catalysts", J. Chem. Eng. Sci. 2001, 56, 4155-4163.
Thompson, et al. "'Sigma-Bond metathesis' for carbon-hydrogen bonds of hydrocarbons and Sc-R (R = H, alkyl, aryl) bonds of permethylscandocene derivatives. Evidence for noninvolvement of the pi system in electrophilic activation of aromatic and vinylic C-H bonds", J. Am. Chem. Soc. 1987, 109, 203-219.
Vidal, "Metathesis of Alkanes Catalyzed by Silica-Supported Transition Metal Hydrides", Science, v 276, issue 5309, Apr. 4, 1997, pp. 99-102. DOI: 10.1126/science.276.5309.99.
Weckhuysen et al., "Alkane dehydrogenation over supported chromium oxide catalysts," Catalysis Today 51 (1999) pp. 223-232.
Welch, et. al., "The Activation Of The Phillips Polymerization Catalyst; II. Activation By Reduction-Reoxidation", J Catalysis, vol. 82, No. 1, Jul. 1, 1983, pp. 110-117.
Zhu, et al., "Synthesis and Structural Characterization of M(PMe3)3(O2CR)2(OH2)H2 (M) Mo, W): Aqua-Hydride Complexes of Molybdenum and Tungsten", Inorg. Chem. 2005, 44, 9637-9639.
International Search Report and Written Opinion issued in corresponding application No. PCT/US2022/032129 dated Dec. 15, 2022, 14 pages.
Allen, et. al., "Analysis of the fluorescent and phosphorescent species in nylon-6,6 in relation to aldol condensation products of cyclopentanone", European Polymer Journal, vol. 21, Issue 6, 1985, pp. 517-526. DOI: 10.1016/0014-3057(85)90075-8.
Borisov Rs et al: "A gas chromatography/mass spectrometry study of the conversion of alicyclic alcohols on membrane-type catalysts using a pulse microreactor implanted into a gas chromatograph injector", Journal Of Analytical Chemistry, Consultants Bureau. New York, US, vol. 71, No. 13, Feb. 7, 2017 (Feb. 7, 2017), pp. 1251-1259, DOI: 10.1134/S1061934816130037.
Ndou et al, "Self-condensation of propanol over solid-base catalysts", Applied Catalysis A: General, vol. 275, No. 1-2, Nov. 8, 2004, pp. 103-110. DOI: 10.1016/J.APCATA.2004.07.025.
Peng Dong et al, "Effective hydrodeoxygenation of dibenzofuran by a bimetallic catalyst in water", New Journal Of Chemistry, vol. 40, No. 2, Dec. 2, 2015 (Dec. 2, 2015), pp. 1605-160. DOI: 10.1039/C5NJ02164B.

\* cited by examiner

CHROMIUM-CATALYZED PRODUCTION OF ALCOHOLS FROM HYDROCARBONS IN THE PRESENCE OF OXYGEN

REFERENCE TO RELATED APPLICATION

This application claims the benefit of U.S. Provisional Patent Application No. 63/208,045, filed on Jun. 8, 2021, the disclosure of which is incorporated herein by reference in its entirety.

FIELD OF THE INVENTION

The present disclosure generally relates to methods for converting hydrocarbons into alcohols and/or carbonyls, and more particularly, relates to performing such methods with chromium catalysts in an oxidizing atmosphere.

BACKGROUND OF THE INVENTION

Alcohol compounds can be prepared by various synthesis techniques from alkanes, but such techniques often require halogens or harsh reaction conditions. Alternative reaction schemes are therefore desirable. Accordingly, it is to these ends that the present invention is generally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Aspects of this invention are directed to processes for converting a hydrocarbon reactant into an alcohol compound and/or a carbonyl compound. In one aspect, the process can comprise (i) irradiating, in an oxidizing atmosphere, the hydrocarbon reactant and a supported chromium catalyst comprising chromium in a hexavalent oxidation state with a light beam at a wavelength in the UV-visible spectrum to reduce at least a portion of the supported chromium catalyst to form a reduced chromium catalyst, and (ii) hydrolyzing the reduced chromium catalyst to form a reaction product comprising the alcohol compound and/or the carbonyl compound. In another aspect, the process can comprise (I) irradiating the hydrocarbon reactant and a supported chromium catalyst comprising chromium in a hexavalent oxidation state with a light beam at a wavelength in the UV-visible spectrum to reduce at least a portion of the supported chromium catalyst to form a reduced chromium catalyst, (II) subjecting the reduced chromium catalyst to an oxidizing atmosphere, and (III) hydrolyzing the reduced chromium catalyst to form a reaction product comprising the alcohol compound and/or the carbonyl compound. In yet another aspect, the process can comprise (a) contacting the hydrocarbon reactant and a supported chromium (II) catalyst to form a treated chromium catalyst, (b) subjecting the treated chromium catalyst to an oxidizing atmosphere, and (c) hydrolyzing the treated chromium catalyst to form a reaction product comprising the alcohol compound and/or the carbonyl compound. A variation of each of these three different processes for converting a hydrocarbon reactant into an alcohol compound and/or a carbonyl compound also is described herein, in which the hydrocarbon reactant can comprise an olefin and the process can be conducted without irradiating with the light beam, and the alcohol and/or carbonyl reaction product can contain an allylic alcohol.

Also provided herein are various supported chromium complexes (or catalyst compositions containing the supported chromium complex) that contain hydrocarbon or hydrocarboxy groups, prior to a hydrolysis step in the disclosed processes. Further, oxygenated oligomer compositions containing oxygenated dimers and trimers of various hydrocarbon reactants also are provided herein.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the catalysts, compositions, processes, or methods described herein are contemplated with or without explicit description of the particular combination. Additionally, unless explicitly recited otherwise, any aspect or feature disclosed herein can be combined to describe inventive catalysts, compositions, processes, or methods consistent with the present disclosure.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

The term "hydrocarbon" whenever used in this specification and claims refers to a compound containing only carbon and hydrogen, whether saturated or unsaturated. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). Non-limiting examples of hydrocarbons include alkanes (linear, branched, and cyclic), alkenes (olefins), and aromatics, among other compounds. Herein, cyclics and aromatics encompass fused ring compounds such as bicyclics and polycyclics.

For any particular compound or group disclosed herein, any name or structure (general or specific) presented is intended to encompass all conformational isomers, regioisomers, stereoisomers, and mixtures thereof that can arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For instance, a general reference to pentane includes n-pentane, 2-methyl-butane, and 2,2-dimethylpropane; and a general reference to a butyl group includes a n-butyl group, a sec-butyl group, an iso-butyl group, and a t-butyl group.

Unless otherwise specified, the term "substituted" when used to describe a group, for example, when referring to a substituted analog of a particular group, is intended to describe any non-hydrogen moiety that formally replaces a hydrogen in that group, and is intended to be non-limiting. Also, unless otherwise specified, a group or groups can also be referred to herein as "unsubstituted" or by equivalent terms such as "non-substituted," which refers to the original group in which a non-hydrogen moiety does not replace a hydrogen within that group. Moreover, unless otherwise specified, "substituted" is intended to be non-limiting and include inorganic substituents or organic substituents as understood by one of ordinary skill in the art.

The terms "contacting" and "combining" are used herein to describe catalysts, compositions, processes, and methods in which the materials or components are contacted or combined together in any order, in any manner, and for any length of time, unless otherwise specified. For example, the materials or components can be blended, mixed, slurried, dissolved, reacted, treated, impregnated, compounded, or otherwise contacted or combined in some other manner or by any suitable method or technique.

"BET surface area" as used herein means the surface area as determined by the nitrogen adsorption Brunauer, Emmett, and Teller (BET) method according to ASTM D1993-91, and as described, for example, in Brunauer, S., Emmett, P. H., and Teller, E., "Adsorption of gases in multimolecular layers," J. Am. Chem. Soc., 60, 3, pp. 309-319, the contents of which are expressly incorporated by reference herein.

In this disclosure, while catalysts, compositions, processes, and methods are described in terms of "comprising" various components or steps, the catalysts, compositions, processes, and methods also can "consist essentially of" or "consist of" the various components or steps, unless stated otherwise.

The terms "a," "an," and "the" are intended to include plural alternatives, e.g., at least one. For instance, the disclosure of "a hydrocarbon reactant," "a solid oxide," etc., is meant to encompass one, or mixtures or combinations of more than one, hydrocarbon reactant, solid oxide, etc., unless otherwise specified.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, when a chemical compound having a certain number of carbon atoms is disclosed or claimed, the intent is to disclose or claim individually every possible number that such a range could encompass, consistent with the disclosure herein. For example, the disclosure that a hydrocarbon reactant contains a $C_1$ to $C_{18}$ alkane compound, or in alternative language, an alkane compound having from 1 to 18 carbon atoms, as used herein, refers to a compound that can have 1, 2, 3, 4, 5, 6, 7, 8, 9, 10, 11, 12, 13, 14, 15, 16, 17, or 18 carbon atoms, as well as any range between these two numbers (for example, a $C_1$ to $C_8$ alkane compound), and also including any combination of ranges between these two numbers (for example, a $C_2$ to $C_4$ alkane compound and a $C_{12}$ to $C_{16}$ alkane compound).

Similarly, another representative example follows for the amount of chromium on the supported chromium catalyst consistent with aspects of this invention. By a disclosure that the amount of chromium can be in a range from 0.1 to 15 wt. %, the intent is to recite that the amount of chromium can be any amount in the range and, for example, can include any range or combination of ranges from 0.1 to 15 wt. %, such as from 0.2 to 10 wt. %, from 0.1 to 5 wt. %, from 0.5 to 2.5 wt. %, or from 5 to 15 wt. %, and so forth. Likewise, all other ranges disclosed herein should be interpreted in a manner similar to these examples.

In general, an amount, size, formulation, parameter, range, or other quantity or characteristic is "about" or "approximate" whether or not expressly stated to be such. Whether or not modified by the term "about" or "approximately," the claims include equivalents to the quantities or characteristics.

Although any methods, devices, and materials similar or equivalent to those described herein can be used in the practice or testing of the invention, the typical methods, devices, and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

The present invention is generally directed to the conversion of a hydrocarbon into an analogous alcohol compound and/or carbonyl compound, where a step in the process in performed in an oxidizing atmosphere.

For instance, a first process irradiates, in an oxidizing atmosphere, a hydrocarbon reactant and a supported chromium (VI) catalyst with a light beam at a wavelength in the UV-visible spectrum, followed by hydrolyzing to form alcohol/carbonyl compounds. If the hydrocarbon reactant is, for example, an olefin such as 1-pentene or 1-hexene, irradiation is not required. A second process irradiates the hydrocarbon reactant and a supported chromium (VI) catalyst with a light beam at a wavelength in the UV-visible spectrum, followed by exposure to an oxidizing atmosphere, and then hydrolyzing to form alcohol/carbonyl products. As above, if the hydrocarbon reactant in the second process is an olefin, irradiation is not required. A third process contacts a hydrocarbon reactant and a supported chromium (II) catalyst (with or without irradiation), followed by exposure to an oxidizing atmosphere, and then hydrolyzing to form alcohol/carbonyl products.

It was expected, due to the well-known ability of oxygen to stop polymerization on Cr-based catalysts, that performing one step in each of these processes in an oxidizing atmosphere would result in no formation of alcohol/carbonyl products. However, instead, these processes provided significant increases in the molar yield of alcohol/carbonyl products (based on the chromium present in the catalyst), as well as producing large amounts of oxygenated oligomers, some of which cannot be formed unless oxygen is present.

Processes for Converting Hydrocarbons into Alcohols

Disclosed herein are processes for converting a hydrocarbon reactant into an alcohol compound and/or a carbonyl compound. A first process can comprise (i) irradiating, in an oxidizing atmosphere, the hydrocarbon reactant and a supported chromium catalyst comprising chromium in a hexavalent oxidation state with a light beam at a wavelength in the UV-visible spectrum to reduce at least a portion of the supported chromium catalyst to form a reduced chromium catalyst, and (ii) hydrolyzing the reduced chromium catalyst to form a reaction product comprising the alcohol compound and/or the carbonyl compound. While not wishing to be bound by theory, it is believed that in step (i), at least a portion of the chromium on the reduced chromium catalyst can have at least one bonding site with a hydrocarboxy group (a —O-hydrocarbon group), which upon hydrolysis in step (ii), can release an alcohol compound and/or carbonyl compound analog of the hydrocarbon compound. The reduced chromium catalyst can have an average oxidation state less than that of the parent supported chromium catalyst. In a variation of the first process in which irradiating is not required, this variation of the first process can comprise (i) contacting, in an oxidizing atmosphere, the hydrocarbon reactant comprising an olefin and a supported chromium catalyst comprising chromium in a hexavalent oxidation state to reduce at least a portion of the supported chromium catalyst to form a reduced chromium catalyst, and (ii) hydrolyzing the reduced chromium catalyst to form a reaction product comprising the alcohol compound and/or the carbonyl compound (e.g., an allylic alcohol). For instance, light treatment is not required for olefins such as 1-pentene and 1-hexene, among others.

A second process for converting a hydrocarbon reactant into an alcohol compound and/or a carbonyl compound can comprise (I) irradiating the hydrocarbon reactant and a supported chromium catalyst comprising chromium in a hexavalent oxidation state with a light beam at a wavelength in the UV-visible spectrum to reduce at least a portion of the supported chromium catalyst to form a reduced chromium catalyst, (II) subjecting the reduced chromium catalyst to an oxidizing atmosphere, and (III) hydrolyzing the reduced chromium catalyst to form a reaction product comprising the alcohol compound and/or the carbonyl compound. As above, it is believed that in step (I), at least a portion of the chromium on the reduced chromium catalyst can have at least one bonding site with a hydrocarboxy group (a —O-hydrocarbon group), and the reduced chromium catalyst in step (I) can have an average oxidation state less than that of the supported chromium catalyst. In a variation of the second process in which irradiating is not required, this variation of the second process can comprise (I) contacting the hydrocarbon reactant comprising an olefin (e.g., 1-pentene and 1-hexene) and a supported chromium catalyst comprising chromium in a hexavalent oxidation state to reduce at least a portion of the supported chromium catalyst to form a reduced chromium catalyst, (II) subjecting the reduced chromium catalyst to an oxidizing atmosphere, and (III) hydrolyzing the reduced chromium catalyst to form a reaction product comprising the alcohol compound and/or the carbonyl compound (e.g., an allylic alcohol).

A third process for converting a hydrocarbon reactant (e.g., an olefin) into an alcohol compound and/or a carbonyl compound can comprise (a) contacting the hydrocarbon reactant (e.g., the olefin) and a supported chromium (II) catalyst to form a treated chromium catalyst, (b) subjecting the treated chromium catalyst to an oxidizing atmosphere, and (c) hydrolyzing the treated chromium catalyst to form a reaction product comprising the alcohol compound and/or the carbonyl compound (e.g., an allylic alcohol). Step (a) in the third process can be performed with or without irradiation.

Generally, the features of the first process, the second process, and the third process (e.g., the hydrocarbon reactant, the supported chromium catalyst, the reduced chromium catalyst, the supported chromium (II) catalyst, the treated chromium catalyst, the light beam, the oxidizing atmosphere, and the conditions under which the irradiating step and the hydrolyzing step are conducted, among others) are independently described herein and these features can be combined in any combination to further describe the disclosed processes to produce alcohol compounds and/or carbonyl compounds. Moreover, additional process steps can be performed before, during, and/or after any of the steps in any of the processes disclosed herein, and can be utilized without limitation and in any combination to further describe these processes, unless stated otherwise. Further, any alcohol compounds and/or carbonyl compounds produced in accordance with the disclosed processes are within the scope of this disclosure and are encompassed herein.

A variety of hydrocarbon reactants can be used in the process to form an alcohol compound and/or a carbonyl compound, inclusive of saturated aliphatic hydrocarbon compounds, unsaturated aliphatic hydrocarbon compounds, linear aliphatic hydrocarbon compounds, branched aliphatic hydrocarbon compounds, and cyclic aliphatic hydrocarbon compounds, as well as combinations thereof. Thus, the hydrocarbon reactant can comprise a linear alkane compound, a branched alkane compound, a cyclic alkane compound, or a combination thereof. Additionally or alternatively, the hydrocarbon reactant can comprise an aromatic compound, such as benzene, toluene, xylene, styrene, and the like, as well as substituted versions thereof, and including combinations thereof. Additionally or alternatively, the hydrocarbon reactant can comprise a linear olefin compound (e.g., an α-olefin), a branched olefin compound, a cyclic olefin compound, or a combination thereof.

Any suitable carbon number hydrocarbon can be used, such that the hydrocarbon reactant can comprise a $C_n$ hydrocarbon compound (and the alcohol compound often can comprise a $C_n$ alcohol compound, and the carbonyl compound often can comprise a $C_n$ carbonyl compound). While not being limited thereto, the integer n can range from 1 to 36 in one aspect, from 1 to 18 in another aspect, from 1 to 12 in yet another aspect, and from 1 to 8 in still another aspect. Accordingly, the hydrocarbon reactant can comprise methane (or ethane), and the alcohol compound can comprise methanol (or ethanol).

Therefore, the hydrocarbon reactant can comprise any suitable carbon number alkane compound, for instance, a $C_1$ to $C_{36}$ alkane compound; alternatively, a $C_1$ to $C_{18}$ alkane compound; alternatively, a $C_1$ to $C_{12}$ alkane compound; or alternatively, a $C_1$ to $C_8$ alkane compound. If desired, the hydrocarbon reactant can contain a single alkane compound of relatively high purity, such as at least 90 wt. % of a single alkane compound, at least 95 wt. % of a single alkane compound, at least 98 wt. % of a single alkane compound, or at least 99 wt. % of a single alkane compound, and so forth. Alternatively, the hydrocarbon reactant can comprise a mixture of two or more hydrocarbon reactants, such as two or more alkane compounds in any relative proportions. Thus, the hydrocarbon reactant can comprise a mixture of $C_1$ to $C_{18}$ alkane compounds, a mixture of $C_1$ to $C_4$ alkane compounds, a mixture of $C_2$ to $C_6$ alkane compounds, a mixture of $C_6$ to $C_8$ alkane compounds, or a mixture of $C_{10}$ to $C_{14}$ alkane compounds, and the like.

Similarly, the hydrocarbon reactant can comprise any suitable carbon number olefin compound, for instance, a $C_2$ to $C_{36}$ olefin compound; alternatively, a $C_2$ to $C_{18}$ olefin compound; alternatively, a $C_2$ to $C_{12}$ olefin compound; or alternatively, a $C_2$ to $C_8$ olefin compound. As above, if desired, the hydrocarbon reactant can contain a single olefin compound of relatively high purity, such as at least 90 wt. % of a single olefin compound, at least 95 wt. % of a single olefin compound, at least 98 wt. % of a single olefin compound, or at least 99 wt. % of a single olefin compound, and so forth. Alternatively, the hydrocarbon reactant can comprise a mixture of two or more hydrocarbon reactants, such as two or more olefin compounds in any relative proportions. Thus, the hydrocarbon reactant can comprise a mixture of $C_2$ to $C_{36}$ olefin compounds, a mixture of $C_2$ to $C_{18}$ olefin compounds, a mixture of $C_2$ to $C_{12}$ olefin compounds, or a mixture of $C_2$ to $C_8$ olefin compounds, and the like.

Likewise, the hydrocarbon reactant can comprise any suitable carbon number aromatic compound, for instance, a $C_6$ to $C_{36}$ aromatic compound; alternatively, a $C_6$ to $C_{18}$ aromatic compound; alternatively, a $C_6$ to $C_{12}$ aromatic compound; or alternatively, a $C_6$ to $C_8$ aromatic compound. As above, if desired, the hydrocarbon reactant can contain a single aromatic compound of relatively high purity, such as at least 90 wt. % of a single aromatic compound, at least 95 wt. % of a single aromatic compound, at least 98 wt. % of a single aromatic compound, or at least 99 wt. % of a single aromatic compound, and so forth. Alternatively, the hydrocarbon reactant can comprise a mixture of two or more hydrocarbon reactants, such as two or more aromatic compounds in any relative proportions. Thus, the hydrocarbon reactant can comprise a mixture of $C_6$ to $C_{36}$ aromatic compounds, a mixture of $C_6$ to $C_{18}$ aromatic compounds, a mixture of $C_6$ to $C_{12}$ aromatic compounds, or a mixture of $C_6$ to $C_8$ aromatic compounds, and the like.

Illustrative examples of alkane, olefin, and aromatic hydrocarbon reactants can include methane, ethane, propane, butane (e.g., n-butane or isobutane), pentane (e.g., n-pentane, neopentane, cyclopentane, or isopentane), hexane, heptane, octane, nonane, decane, undecane, dodecane, tridecane, tetradecane, pentadecane, hexadecane, heptadecane, octadecane, ethylene, propylene, 1-butene, 1-pentene, 2-pentene, 1-hexene, 1-heptene, 1-octene, 1-decene, 1-dodecene, 1-tetradecene, 1-hexadecene, 1-octadecene, cyclopentene, cyclohexene, benzene, toluene, ethylbenzene, xylene, styrene, mesitylene, and the like, as well as combinations thereof.

Thus, the hydrocarbon reactant can comprise a mixture of an aliphatic hydrocarbon and an aromatic hydrocarbon. In a non-limiting aspect, the hydrocarbon reactant can comprise methane; alternatively, ethane; alternatively, propane; alternatively, butane; alternatively, pentane; alternatively, hexane; alternatively, heptane; alternatively, octane; alternatively, nonane; alternatively, decane; alternatively, undecane; alternatively, dodecane; alternatively, tridecane; alternatively, tetradecane; alternatively, pentadecane; alternatively, hexadecane; alternatively, heptadecane; alternatively, octadecane; alternatively, ethylene; alternatively, propylene; alternatively, 1-butene; alternatively, 1-pentene; alternatively, 1-hexene; alternatively, 1-heptene; alternatively, 1-octene; alternatively, 1-decene; alternatively, 1-dodecene; alternatively, 1-tetradecene; alternatively, 1-hexadecene; alternatively, 1-octadecene; alternatively, cyclopentene; alternatively, cyclohexene; alternatively, benzene; alternatively, toluene; alternatively, ethylbenzene; alternatively, xylene; alternatively, styrene; or alternatively, mesitylene.

In an aspect, the hydrocarbon (alkane) reactant can comprise methane, ethane, propane, n-butane, isobutane, n-pentane, neopentane, isopentane, n-hexane, n-heptane, n-octane, n-decane, n-dodecane, and the like, or any combination thereof, while in another aspect, the hydrocarbon (alkane) reactant can comprise methane, ethane, propane, butane, pentane, hexane, and the like, or any combination thereof. In yet another aspect, the hydrocarbon (olefin) reactant can comprise ethylene, propylene, 1-butene, 1-pentene, 2-pentene, 1-hexene, 1-heptene, 1-octene, 1-decene, 1-dodecene, 1-tetradecene, 1-hexadecene, 1-octadecene, cyclopentene, cyclohexene, and the like, or any combination thereof, or alternatively, ethylene, propylene, 1-butene, 1-pentene, 1-hexene, 1-heptene, 1-octene, or any combination thereof. In still another aspect, the hydrocarbon (aromatic) reactant can comprise benzene, toluene, ethylbenzene, xylene, mesitylene, styrene, 4-phenyl-1-butene, and the like, or any combination thereof.

Generally, in the first process, the second process, and the third process, the irradiating step or the contacting step can be performed under any conditions sufficient to accommodate the irradiation of or contacting of the hydrocarbon reactant and the supported chromium catalyst (comprising chromium in a hexavalent oxidation state) to form the reduced chromium catalyst (having a lower oxidation state) or the contacting of the hydrocarbon reactant and the supported chromium (II) catalyst to form the treated catalyst. For instance, the relative amount (or concentration) of the hydrocarbon reactant to the amount of chromium (in the supported chromium catalyst or the supported chromium (II) catalyst) can alter the efficacy of the reduction process. In certain aspects, the molar ratio of the hydrocarbon reactant to the chromium (in the supported chromium catalyst or the supported chromium (II) catalyst) can be at least 0.25:1, at least 0.5:1, at least 1:1, at least 10:1, at least 100:1, at least 1000:1, or at least 10,000:1. Thus, a large excess of the hydrocarbon reactant can be used, and there is no particular limit as to the maximum amount of hydrocarbon reactant.

Likewise, the molar ratio of elemental oxygen or other oxidizing agent to chromium (of the supported chromium catalyst, of the reduced chromium catalyst, or of the treated chromium catalyst, as the context requires for the respective process) is not particularly limited, but often can be at least 0.25:1, at least 0.5:1, at least 1:1, at least 10:1, at least 100:1, at least 1000:1, or at least 10,000:1. Thus, a large excess of the elemental oxygen or other oxidizing agent can be used, and there is no particular limit as to the maximum amount of elemental oxygen or other oxidizing agent in the oxidizing atmosphere. For instance, a large molar excess of air can be used in these processes.

In the first and second processes, the temperature and pressure of the irradiating step (or contacting step) can be such that the hydrocarbon reactant remains a liquid throughout reduction of the supported chromium catalyst in one aspect, and the hydrocarbon remains a gas throughout reduction of the supported chromium catalyst in another aspect. Advantageously, it was found that reducing supported chromium compounds at lower temperatures than those typically required to reduce hexavalent chromium species using heat and not light, was possible by the irradiating steps disclosed herein. In certain aspects, the irradiating step (or the contacting step) can be conducted at a temperature of less than 200° C., less than 100° C., less than 70° C., less than 40° C., from 0° C. to 200° C., from −100° C. to 100° C., from 0° C.

to 100° C., or from 10° C. to 40° C., and can produce a reduced chromium catalyst (e.g., with at least a portion of the chromium on the reduced chromium catalyst having at least one bonding site with a hydrocarboxy group). These temperature ranges also are meant to encompass circumstances where the irradiation or the contacting is performed at a series of different temperatures, instead of at a single fixed temperature, falling within the respective temperature ranges, wherein at least one temperature is within the recited ranges.

The irradiating step can be further characterized by an amount of time that the hydrocarbon reactant and supported chromium catalyst are exposed to the light beam, e.g., an exposure time. Without being bound by theory, it is believed that exposure to the light beam in the presence of the hydrocarbon reactant is responsible for the reduction of the supported chromium catalyst, and therefore it follows that the exposure time must be sufficient to allow this transformation to occur, whether the transformation occurs very rapidly or very slowly. Likewise, the contacting step can be further characterized by the amount of time that the hydrocarbon reactant and supported chromium catalyst are contacted, e.g., a contact time. Thus, in certain aspects, and not being limited thereto, the exposure time (or the contact time) can be in a range from 15 sec to 48 hr, from 15 sec to 24 hr, from 1 hr to 8 hr, from 15 min to 4 hr, from 1 min to 6 hr, from 5 min to 1 hr, from 10 min to 2 hr, from 1 min to 1 hr, or from 1 min to 15 min. As one of skill in the art would recognize, the exposure time can vary based on the intensity of the light beam, the wavelength(s) of the light beam, and so forth. Agitation, mixing, or other suitable technique can be used to ensure that the mixture of the supported chromium catalyst (e.g., particles) and the hydrocarbon reactant is uniformly contacted and/or exposed to the light beam irradiation.

The supported chromium catalyst and the hydrocarbon reactant can be continuously subjected to irradiation (for the entirety of the exposure time), or the irradiation can be pulsed (such that the total of the pulses equates to the exposure time, e.g., sixty 1-sec pulses equates to a 60-sec exposure time). Combinations of periods of continuous irradiation and pulsed irradiation can be utilized, if desired.

In the disclosed processes, irradiation of a supported chromium catalyst with a light beam in the UV-visible spectrum, in the presence of a hydrocarbon reactant, results in a chromium catalyst with a reduced oxidation state (e.g., a reduced chromium catalyst). A wide range of wavelengths, light sources, and intensities can be used, as long as these wavelengths, light sources, and intensities are sufficient to reduce at least a portion of the hexavalent chromium species present in the supported chromium catalyst. In certain aspects, for instance, the light can be derived from any suitable source, such as from sunlight, a fluorescent white light, an LED diode, and/or a UV lamp. The distance from non-sunlight sources can be varied as needed (e.g., minimized) to increase the effectiveness of the irradiation.

The wavelength of the light can be any in the range of UV-visible light. In certain aspects, the wavelength of the light beam can be a single wavelength, or more than one wavelength, such as a range of wavelengths. For instance, the wavelength of the light beam can be a range of wavelengths spanning at least 25 nm, at least 50 nm, at least 100 nm, at least 200 nm, or at least 300 nm. In one aspect, the wavelength of the light beam can comprise a single wavelength or a range of wavelengths in the UV spectrum, in the visible spectrum (from 380 nm to 780 nm), or both. In another aspect, the wavelength of the light beam can comprise a single wavelength or a range of wavelengths in the 200 nm to 750 nm range. Yet, in another aspect, the wavelength of the light beam can comprise a single wavelength or a range of wavelengths in the 300 to 750 nm range, the 350 nm to 650 nm range, the 300 nm to 600 nm range, the 300 nm to 500 nm range, or the 400 nm to 500 nm range. In other aspects, the wavelength of the light beam can comprise a single wavelength or a range of wavelengths below 600 nm, below 525 nm, or below 500 nm; additionally or alternatively, above 300 nm, above 350 nm, above 400 nm, or above 450 nm. Beneficially, blue light and UV light sources are typically more effective, thus the wavelength of the light beam can comprise a single wavelength or a range of wavelengths below 475 nm; alternatively, below 450 nm; alternatively, below 430 nm; or alternatively, below 420 nm; and additionally or alternatively, above 350 nm; alternatively, above 370 nm; alternatively, above 380 nm; or alternatively, above 400 nm.

The light beam of the irradiating step also can be characterized by its intensity (e.g., the total amount of light emitted from a source). In certain aspects, the light beam can have an intensity of at least 500 lumens, at least 1,000 lumens, at least 2,000 lumens at least 5,000 lumens, at least 10,000 lumens, at least 20,000 lumens, at least 50,000 lumens, or at least 100,000 lumens. Thus, there may not be an upper limit on the intensity of the light source. Alternatively, the light beam can have an intensity in a range from 50 to 50,000 lumens, from 50 to 10,000 lumens, from 100 to 5,000 lumens, or from 500 to 2,000 lumens. Additionally, the light beam can be characterized by the amount of light reaching the hydrocarbon reactant and supported chromium catalyst, i.e., the flux. In certain aspects, the hydrocarbon reactant and the supported chromium catalyst comprising chromium in a hexavalent oxidation state can be irradiated by at least 100 lux, at least 500 lux, at least 1000 lux, at least 2000 lux, at least 5000 lux, at least 10,000 lux, at least 20,000 lux, at least 50,000 lux, at least 100,000 lux, or in a range from 10,000 to 1,000,000 lux, from 10,000 to 250,000 lux, from 10,000 to 100,000 lux, from 20,000 to 200,000 lux, from 20,000 to 100,000 lux, from 50,000 to 500,000 lux, or from 50,000 to 200,000 lux.

Additionally or alternatively, in certain aspects, the hydrocarbon reactant and the supported chromium catalyst comprising chromium in the hexavalent oxidation state can be irradiated with a light beam from a light source having a power of at least 50 watts, at least 100 watts, at least 200 watts, at least 500 watts, at least 1,000 watts, or at least 2,000 watts.

Any suitable reactor or vessel can be used to form the alcohol compound and/or the carbonyl compound, non-limiting examples of which can include a flow reactor, a continuous reactor, a packed bed reactor, a fluidized bed reactor, and a stirred tank reactor, including more than one reactor in series or in parallel, and including any combination of reactor types and arrangements.

In one aspect, the hydrocarbon reactant can be in a gas phase during the irradiating step (or contacting step). In another aspect, the hydrocarbon reactant can be in a liquid phase during the irradiating step (or contacting step). In another aspect, the disclosed processes can comprise irradiating (or contacting) a slurry (e.g., a loop slurry) of the solid supported chromium catalyst in the hydrocarbon reactant. In yet another aspect, the disclosed processes can comprise contacting the hydrocarbon reactant with a fluidized bed of the solid supported chromium catalyst, and irradiating while contacting (fluidizing). In still another aspect, the disclosed processes can comprise contacting the hydrocarbon reactant (e.g., in the gas phase or in the liquid phase) with a fixed bed of the solid supported chromium catalyst, and irradiating while contacting. As a skilled artisan would recognize, there are other methods for contacting the hydrocarbon reactant and the solid supported chromium catalysts and irradiating, and the disclosed processes are not limited solely to those disclosed herein. For instance, the hydrocarbon reactant and the supported chromium catalyst can be mixed or contacted in a stirred tank, and irradiated while being mixed in the stirred tank.

Any suitable pressure can be used to contact the hydrocarbon reactant and the supported catalyst and to form the reduced chromium catalyst, and such can depend upon the carbon number of the hydrocarbon reactant (and its boiling point), the type of reactor configuration and desired mode for contacting the hydrocarbon reactant with the (solid) supported chromium catalyst, among other considerations.

Often, the process for forming the reduced chromium catalyst (and subsequently, the alcohol and/or carbonyl compound) can be a flow process and/or a continuous process. In such circumstances, the hydrocarbon reactant-supported chromium catalyst contact time (or reaction time) can be expressed in terms of weight hourly space velocity (WHSV)—the ratio of the weight of the hydrocarbon reactant which comes in contact with a given weight of the supported chromium catalyst per unit time (units of g/g/hr, or $hr^{-1}$).

While not limited thereto, the WHSV employed for the disclosed processes can have a minimum value of 0.01 $hr^{-1}$, 0.02 $hr^{-1}$, 0.05 $hr^{-1}$, 0.1 $hr^{-1}$, 0.25 $hr^{-1}$, or 0.5 $hr^{-1}$; or alternatively, a maximum value of 500 $hr^{-1}$, 400 $hr^{-1}$, 300 $hr^{-1}$, 100 $hr^{-1}$, 50 $hr^{-1}$, 10 $hr^{-1}$, 5 $hr^{-1}$, 2 $hr^{-1}$, or 1 $hr^{-1}$. Generally, the WHSV can be in a range from any minimum WHSV disclosed herein to any maximum WHSV disclosed herein. In a non-limiting aspect, the WHSV can be in a range from 0.01 $hr^{-1}$ to 500 $hr^{-1}$; alternatively, from 0.01 $hr^{-1}$ to 10 $hr^{-1}$; alternatively, from 0.01 $hr^{-1}$ to 1 $hr^{-1}$; alternatively, from 0.02 $hr^{-1}$ to 400 $hr^{-1}$; alternatively, from 0.02 $hr^{-1}$ to 50 $hr^{-1}$; alternatively, from 0.05 $hr^{-1}$ to 300 $hr^{-1}$; alternatively, from 0.05 $hr^{-1}$ to 5 $hr^{-1}$; alternatively, from 0.1 $hr^{-1}$ to 400 $hr^{-1}$; alternatively, from 0.25 $hr^{-1}$ to 50 $hr^{-1}$; alternatively, from 0.25 $hr^{-1}$ to 2 $hr^{-1}$; alternatively, from 0.5 $hr^{-1}$ to 400 $hr^{-1}$; alternatively, from 0.5 $hr^{-1}$ to 5 $hr^{-1}$; or alternatively, from 0.5 $hr^{-1}$ to 2 $hr^{-1}$. Other WHSV ranges are readily apparent from this disclosure.

Referring now to the second process, step (II) is directed to subjecting the reduced chromium catalyst to an oxidizing atmosphere. This step of subjecting the reduced chromium catalyst to an oxidizing atmosphere generally can be performed, independently, under the same temperature, pressure, time, and method of contacting (e.g., fixed bed or fluidized bed) conditions described herein for the contacting and irradiating steps (step (i) of the first process and step (I) of the second process).

Referring now the third process, step (a) is directed to contacting the hydrocarbon reactant and the supported chromium (II) catalyst to form the treated chromium catalyst (with or without irradiation), and step (b) is directed to subjecting the treated chromium catalyst to the oxidizing atmosphere. Step (a) and step (b) generally can be performed, independently, under the same temperature, pressure, time, WHSV, and method of contacting (e.g., fixed bed or fluidized bed) conditions described herein for the contacting and irradiating steps (step (i) of the first process and step (I) of the second process).

The oxidizing atmosphere in the first process, the second process, and the third process is not particular limited. Typical materials used to create the oxidizing atmosphere include, but are not limited to, oxygen, air, a mixture of air and an inert gas (such as nitrogen), a mixture of oxygen and an inert gas, NO, $NO_2$, $N_2O$, ozone, a halide oxide, $H_2O_2$, an organic peroxide, and the like, as well as combinations thereof. For convenience, air is often used, and thus the respective chromium catalyst in the first process, the second process, and the third process can be simply subjected to or exposed to air under any suitable conditions.

Referring now to the hydrolyzing steps, in which the reduced chromium catalyst in the first process (e.g., with at least a portion of the chromium on the reduced chromium catalyst having at least one bonding site with a hydrocarboxy group) is hydrolyzed to form a reaction product comprising the alcohol compound and/or the carbonyl compound, and in which the reduced chromium catalyst in the second process is hydrolyzed to form a reaction product comprising the alcohol compound and/or the carbonyl compound, and in which the treated chromium catalyst in the third process is hydrolyzed to form a reaction product comprising the alcohol compound and/or the carbonyl compound. Generally, the temperature, pressure, and time features, independently, of these hydrolyzing steps can be the same as those disclosed herein for the irradiating step (or contacting step), although not limited thereto. For example, the hydrolyzing step can be conducted at a temperature of less than 200° C., less than 100° C., less than 70° C., less than 40° C., from 0° C. to 200° C., from 0° C. to 100° C., or from 10° C. to 40° C., and can result in the formation of a reaction product containing the alcohol compound and/or the carbonyl compound. These temperature ranges also are meant to encompass circumstances where the hydrolyzing step is performed at a series of different temperatures, instead of at a single fixed temperature, falling within the respective temperature ranges, wherein at least one temperature is within the recited ranges.

While not limited thereto, the hydrolyzing step can comprise contacting the reduced chromium catalyst (or the treated chromium catalyst) with a hydrolysis agent. Illustrative and non-limiting examples of suitable hydrolysis agents can include water, steam, an alcohol agent, an acid agent, an alkaline agent, and the like, as well as combinations thereof. Thus, mixtures of water and various alcohol agents, such as $C_1$-$C_4$ alcohols (and/or acid agents, such as hydrochloric acid, sulfuric acid, acetic acid, ascorbic acid, and the like; and/or alkaline agents, such as sodium hydroxide, ammonium hydroxide, and the like) in any relative proportions can be used as the hydrolysis agent. Thus, the pH of the hydrolysis agent(s) can range from acid to neutral to basic pH values, generally encompassing a pH range from 1 (or less) to 13.

Optionally, the hydrolysis agent can further comprise any suitable reducing agent, and representative reducing agents include ascorbic acid, iron (II) reducing agents, zinc reducing agents, and the like, as well as combinations thereof. Often, the reducing agent can comprise sodium bisulfite, sodium thiosulfate, sodium sulfide, ascorbic acid, ferrous (II) ions, and the like, or any combination thereof. These are sometimes useful for preventing unwanted secondary oxidations by unreacted chromium (VI) or other chromium species. Further, they also can be used to tailor the product range by increasing selectivity. For example, in some aspects, adding reducing agents to the hydrolysis agent can eliminate all carbonyl products and instead produce only alcohol products. For instance, in the examples that follow, a reducing agent is added in some examples to the final quench solution in order to produce more alcohol products and less carbonyl products (e.g., to prevent secondary oxidation of the alcohols formed).

As disclosed herein, the reaction product can comprise an alcohol compound and/or a carbonyl compound, which can be an analog of the hydrocarbon reactant. Thus, typical alcohol compounds that can be synthesized using the processes disclosed herein can include, for instance, methanol, ethanol, isopropanol, butanols, pentanols, hexanols, heptanols, octanols, nonanols, decanols, undecanols, dodecanols, tridecanols, tetradecanols, pentadecanols, hexadecanols, heptadecanols, octadecanols, benzyl alcohol, phenols, xylenols, and the like, as well as combinations thereof. Herein, an alcohol compound encompasses monoalcohol compounds as well as diol compounds (e.g., ethanediol and hexanediols). Thus, the alcohol compound can comprise a diol, an allylic alcohol, a phenol, and the like, as well as any combination thereof.

In addition to or in lieu of the alcohol compound, the reaction product can comprise a carbonyl compound, such as an aldehyde compound, a ketone compound, or an organic acid compound, as well as any combination of aldehyde, ketone, and organic acid compounds. Thus, enols are encompassed herein, since the reaction product can comprise an alcohol compound, a carbonyl compound, or both. In some aspects, the alcohol or carbonyl product can contain unsaturation. For example, the carbon(s) adjacent to the alcohol or carbonyl group can contain a double bond. While not wishing to be bound by theory, it is believed that the allyl C—H bond is particularly susceptible to being attacked by the chromium (VI) or other chromium species. Thus, when the reductant hydrocarbon has a double bond, a typical alcohol product, and often among the most abundant, contains the —OH group on the adjacent allyl carbon. The alcohol compound in some aspects, therefore, can be an allylic alcohol such as a $C_4$-$C_8$ allylic alcohol. Non-limiting examples of allylic alcohols that can be prepared herein include 1-hexen-3-ol, 2-hexen-1-ol, 1-penten-3-ol, 2-penten-1-ol, 1-cyclohexen-3-ol, and the like, as well as combinations thereof.

The processes described herein result in an unexpectedly high conversion of the hydrocarbon reactant and/or yield to the alcohol compound (or carbonyl compound). In one aspect, the minimum conversion (or yield) can be at least 2 wt. %, at least 5 wt. %, at least 10 wt. %, at least 15 wt. %, or at least 25 wt. % of the feedstock hydrocarbon. Additionally, the maximum conversion (or yield) can be 50 wt. %, 70 wt. %, 80 wt. %, 90 wt. %, 95 wt. %, or 99 wt. %, and can approach 100% conversion of the hydrocarbon reactant (or yield of the alcohol compound, or yield of the carbonyl compound). Generally, the conversion (or yield) can be in a range from any minimum conversion (or yield) disclosed herein to any maximum conversion (or yield) disclosed herein. Non-limiting ranges of conversion (or yield) can include from 5 wt. % to 99 wt. %, from 10 wt. % to 95 wt. %, or from 15 wt. % to 70 wt. %. For conversion, the percentages are the amount of the hydrocarbon reactant converted based on the initial amount of the hydrocarbon reactant. The yield values are weight percentages, and are based on the weight of the alcohol compound (or carbonyl compound) produced to the weight of hydrocarbon reactant. In some aspects, these conversions (or yields) can be achieved in a batch process, while in other aspects, these conversions (or yields) can be achieved in a flow or continuous process, such as, for example, a single pass or multiple passes through a reactor (e.g., a fixed bed reactor). Often, the conversion and yield can be manipulated by varying the ratio of reductant hydrocarbon feed to the amount of chromium (VI) or chromium (II), the amount of oxygen in the oxidizing atmosphere, and by varying other reaction conditions such as time, temperature, and irradiation.

Also unexpectedly, continuous flow processes for producing the alcohol compound and/or carbonyl compound in accordance with this invention have unexpectedly high single pass conversions of the hydrocarbon reactant (or single pass yields to the desired alcohol or carbonyl compound). In one aspect, the minimum single pass conversion (or yield) can be at least 2 wt. %, at least 5 wt. %, at least 10 wt. %, at least 15 wt. %, or at least 25 wt. %. Additionally, the maximum single pass conversion (or yield) can be 50 wt. %, 70 wt. %, 80 wt. %, 90 wt. %, 95 wt. %, or 99 wt. %, and can approach 100% conversion of the hydrocarbon reactant (or yield of the alcohol compound, or yield of the carbonyl compound), depending upon the reaction conditions. Generally, the single pass conversion (or yield) can be in a range from any minimum single pass conversion (or yield) disclosed herein to any maximum single pass conversion (or yield) disclosed herein. Non-limiting ranges of single pass conversion (or yield) can include from 5 wt. % to 99 wt. %, from 10 wt. % to 95 wt. %, or from 15 wt. % to 70 wt. %.

In the first and second processes, the yield of the alcohol compound (or carbonyl compound) also can be characterized based on the amount of chromium (VI) (of the supported chromium catalyst). For instance, the molar ratio (molar yield) of the alcohol compound (or carbonyl compound) based on the moles of chromium (VI) can be at least 0.025 moles, at least 0.05 moles, at least 0.1 moles, at least 0.25 moles, at least 0.5 moles, or at least 0.75 moles. While not limited thereto, the yield in moles of product per mole of Cr(VI) often can be up to 10 moles, up to 8 moles, up to 5 moles, up to 3 moles, up to 2 moles, up to 1.5 moles, or up to 1 mole of the alcohol compound (or carbonyl compound) per mole of chromium (VI). If more than one alcohol compound and/or carbonyl compound is/are produced, then this ratio represents the total moles of alcohol and/or carbonyl compounds produced per mole of chromium (VI).

Similarly, in the third process, the yield of the alcohol compound (or carbonyl compound) also can be characterized based on the amount of chromium (II) (of the supported chromium (II) catalyst). For instance, the molar ratio (molar yield) of the alcohol compound (or carbonyl compound) based on the moles of chromium (II) can be at least 0.01 moles, at least 0.025 moles, at least 0.05 moles, at least 0.1 moles, at least 0.25 moles, at least 0.5 moles, or at least 0.75 moles. While not limited thereto, the yield in moles of product per mole of Cr(II) often can be up to 10 moles, up to 8 moles, up to 5 moles, up to 3 moles, up to 2 moles, up to 1.5 moles, or up to 1 mole of the alcohol compound (or carbonyl compound) per mole of chromium (II). As above, if more than one alcohol compound and/or carbonyl compound is/are produced, then this ratio represents the total moles of alcohol and/or carbonyl compounds produced per mole of chromium (II).

The processes to produce the alcohol compounds and/or carbonyl compounds disclosed herein typically can result in—after hydrolysis—a crude reaction mixture containing residual hydrocarbon reactant (e.g., methane), a desired alcohol compound and/or carbonyl compound (e.g., methanol), solvent (if used), and by-products. In many instances, it can be desirable to isolate or separate at least a portion (and in some cases, all) of the hydrocarbon reactant from the reaction product after the hydrolyzing step. This can be accomplished using any suitable technique, which can include but is not limited to, extraction, filtration, evaporation, or distillation, as well as combinations of two or more of these techniques. In particular aspects of this invention, the isolating or separating step utilizes distillation at any suitable pressure (one or more than one distillation column can be used).

Additionally or alternatively, the processes disclosed herein can further comprise a step of separating at least a portion (and in some cases, all) of the alcohol compound (or carbonyl compound) from the reaction product, and any suitable technique can be used, such as extraction, filtration, evaporation, distillation, or any combination thereof. Additionally or alternatively, the processes disclosed herein can further comprise a step of separating at least a portion (and in some cases, all) of the reduced chromium catalyst (or the treated chromium catalyst) from the reaction product after hydrolyzing, and as above, any suitable technique(s) can be used.

Optionally, certain components of the reaction product—such as the hydrocarbon reactant—can be recovered and recycled to the reactor. In such instances, at least a portion (and in some cases, all) of the hydrocarbon reactant can be recycled and contacted with the supported chromium catalyst again (or the supported chromium (II) catalyst again), such that the overall conversion of the hydrocarbon product is increased after multiple contacts with the chromium catalyst (or multiple passes through the reactor containing the chromium catalyst).

If desired, the first and second processes disclosed herein can further comprise a step of calcining at least a portion (and in some cases, all) of the reduced chromium catalyst to regenerate the supported chromium catalyst. Any suitable calcining conditions can be used, for instance, subjecting the reduced chromium catalyst to an oxidizing atmosphere at any suitable peak temperature and time conditions, such as a peak temperature from 300° C. to 1000° C., from 500° C. to 900° C., or from 550° C. to 870° C., for a time period of from 1 min to 24 hr, from 1 hr to 12 hr, or from 30 min to 8 hr.

The calcining step can be conducted using any suitable technique and equipment, whether batch or continuous. For instance, the calcining step can be performed in a belt calciner or, alternatively, a rotary calciner. In some aspects, the calcining step can be performed in a batch or continuous calcination vessel comprising a fluidized bed. As would be recognized by those of skill in the art, other suitable techniques and equipment can be employed for the calcining step, and such techniques and equipment are encompassed herein.

If desired, the third process disclosed herein can further comprise a step of reducing at least a portion (and in some cases, all) of the treated chromium catalyst to regenerate the supported chromium (II) catalyst. Any suitable reducing conditions can be used, for instance, subjecting the treated chromium catalyst to a reducing atmosphere, e.g., CO reduction, UV light reduction, elevated temperature reduction, or any combination thereof. As an example, the treated chromium catalyst can be contacted with CO at 150-800° C. to form the supported chromium (II) catalyst. Another suitable method is to contact the treated chromium catalyst with light and CO at lower temperatures (e.g., 25° C.) to reduce Cr(VI) and other valent chromium species to chromium (II). Hydrogen also can be used at elevated temperature instead of CO, if desired. This invention is not limited by the method for forming the supported chromium (II) catalyst, as there are other methods for forming chromium (II) readily known to a skilled artisan.

Chromium Catalysts

Generally, the first process and the second process are applicable to the reduction of any hexavalent chromium catalyst, and are not limited to the reduction of any particular type of supported chromium catalyst comprising chromium in a hexavalent oxidation state. Thus, supported chromium catalysts contemplated herein encompass those prepared by contacting a support with a chromium-containing compound—representative and non-limiting examples of the chromium-compound compound include chromium (III) acetate, basic chromium (III) acetate, chromium (III) acetylacetonate, $Cr_2(SO_4)_3$, $Cr(NO_3)_3$, and $CrO_3$—and calcining in an oxidizing atmosphere to form a supported chromium catalyst. In these aspects, chromium can be impregnated during, or prior to, the calcination step, which can be conducted at a variety of temperatures and time periods, and can be generally selected to convert all or a portion of the chromium to hexavalent chromium. The irradiation or contacting steps disclosed herein can comprise reducing at least a portion of the hexavalent chromium species to a reduced oxidation state—for instance, Cr (II) and/or Cr (III) and/or Cr (IV) and/or Cr (V) species, any of which may be present on the reduced chromium catalyst.

Any suitable chromium-containing compound (or chromium precursor) can be used as a chromium component to prepare the supported chromium catalyst. Illustrative and non-limiting examples of chromium (II) compounds can include chromium (II) acetate, chromium (II) chloride, chromium (II) bromide, chromium (II) iodide, chromium (II) sulfate, and the like, as well as combinations thereof. Likewise, illustrative and non-limiting examples of chromium (III) compounds can include a chromium (III) carboxylate, a chromium (III) naphthenate, a chromium (III) halide, chromium (III) sulfate, chromium (III) nitrate, a chromium (III) dionate, and the like, as well as combinations thereof. In some aspects, the chromium-containing compound can comprise chromium (III) acetate, chromium (III) acetylacetonate, chromium (III) chloride, chromium (III) bromide, chromium (III) sulfate, chromium (III) nitrate, and the like, as well as combinations thereof.

While not required, it can be beneficial for the chromium-containing compound to be soluble in a hydrocarbon solvent during preparation of the supported chromium catalyst. In such situations, the chromium-containing compound can comprise tertiary butyl chromate, a diarene chromium (0) compound, bis-cyclopentadienyl chromium (II), chromium (III) acetylacetonate, chromium acetate, and the like, or any combination thereof. Similarly, and not required, it can be beneficial for the chromium-containing compound to be soluble in water during preparation of the supported chromium catalyst. In such situations, the chromium-containing compound can comprise chromium trioxide, chromium acetate, chromium nitrate, and the like, or any combination thereof.

Other examples include sodium, potassium, or ammonium chromate or dichromate, which is unexpected, because such alkali metal chromates are not usually acceptable for use in polymerization catalysts because of low activity and sintering of the solid support. Thus, the chromium precursor can comprise a chromate compound, e.g., potassium chromate, sodium chromate, ammonium chromate, potassium dichromate, sodium dichromate, ammonium dichromate, and the like, as well as any combination thereof. Since chromium in already in the hexavalent state for these chromate compounds, heat treatment options other than traditional calcining in an oxidizing atmosphere can be used, such as low temperatures (and even an inert atmosphere) to dry or remove excess water/moisture prior to exposing the supported chromium catalyst to light irradiation.

Referring now to the first process, the second process, and the third process, various solid supports can be used for the supported chromium catalyst (or the reduced chromium catalyst, or the supported chromium (II) catalyst, or the treated chromium catalyst), such as conventional solid oxides and zeolites. Generally, the solid oxide can comprise oxygen and one or more elements selected from Group 2, 3, 4, 5, 6, 7, 8, 9, 10, 11, 12, 13, 14, or 15 of the periodic table, or comprise oxygen and one or more elements selected from the lanthanide or actinide elements (See: Hawley's Condensed Chemical Dictionary, 11$^{th}$ Ed., John Wiley & Sons, 1995; Cotton, F. A., Wilkinson, G., Murillo, C. A., and Bochmann, M., Advanced Inorganic Chemistry, 6$^{th}$ Ed., Wiley-Interscience, 1999). For example, the solid oxide can comprise oxygen and an element, or elements, selected from Al, B, Be, Bi, Cd, Co, Cr, Cu, Fe, Ga, La, Mn, Mo, Ni, Sb, Si, Sn, Sr, Th, Ti, V, W, P, Y, Zn, and Zr. Illustrative examples of solid oxide materials or compounds that can be used as solid support can include, but are not limited to, $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, and the like, including mixed oxides thereof, and combinations thereof.

The solid oxide can encompass oxide materials such as silica, alumina, or titania, "mixed oxide" compounds thereof such as silica-titania, and combinations or mixtures of more than one solid oxide material. Mixed oxides such as silica-titania can be single or multiple chemical phases with more than one metal combined with oxygen to form the solid oxide. Examples of mixed oxides that can be used as solid oxide include, but are not limited to, silica-alumina, silica-coated alumina, silica-titania, silica-zirconia, alumina-titania, alumina-zirconia, zinc-aluminate, alumina-boria, silica-boria, aluminum phosphate, aluminophosphate, aluminophosphate-silica, titania-zirconia, and the like, or a combination thereof. In some aspects, the solid support can comprise silica, silica-alumina, silica-coated alumina, silica-titania, silica-titania-magnesia, silica-zirconia, silica-magnesia, silica-boria, aluminophosphate-silica, and the like, or any combination thereof. Silica-coated aluminas are encompassed herein; such oxide materials are described in, for example, U.S. Pat. Nos. 7,884,163 and 9,023,959, incorporated herein by reference in their entirety.

The percentage of each oxide in a mixed oxide can vary depending upon the respective oxide materials. As an example, a silica-alumina (or silica-coated alumina) typically has an alumina content from 5 wt. % to 95 wt. %. According to one aspect, the alumina content of the silica-alumina (or silica-coated alumina) can be from 5 wt. % alumina 50 wt. % alumina, or from 8 wt. % to 30 wt. % alumina. In another aspect, high alumina content silica-aluminas (or silica-coated aluminas) can be employed, in which the alumina content of these materials typically ranges from 60 wt. % alumina to 90 wt. % alumina, or from 65 wt. % alumina to 80 wt. % alumina.

In one aspect, the solid oxide can comprise silica-alumina, silica-coated alumina, silica-titania, silica-zirconia, alumina-titania, alumina-zirconia, zinc-aluminate, alumina-boria, silica-boria, aluminum phosphate, aluminophosphate, aluminophosphate-silica, titania-zirconia, or a combination thereof; alternatively, silica-alumina; alternatively, silica-coated alumina; alternatively, silica-titania; alternatively, silica-zirconia; alternatively, alumina-titania; alternatively, alumina-zirconia; alternatively, zinc-aluminate; alternatively, alumina-boria; alternatively, silica-boria; alternatively, aluminum phosphate; alternatively, aluminophosphate; alternatively, aluminophosphate-silica; or alternatively, titania-zirconia.

In another aspect, the solid oxide can comprise silica, alumina, titania, thoria, stania, zirconia, magnesia, boria, zinc oxide, a mixed oxide thereof, or any mixture thereof. In yet another aspect, the solid support can comprise silica, alumina, titania, or a combination thereof; alternatively, silica; alternatively, alumina; alternatively, titania; alternatively, zirconia; alternatively, magnesia; alternatively, boria; or alternatively, zinc oxide. In still another aspect, the solid oxide can comprise silica, alumina, silica-alumina, silica-coated alumina, aluminum phosphate, aluminophosphate, heteropolytungstate, titania, zirconia, magnesia, boria, zinc oxide, silica-titania, silica-yttria, silica-zirconia, alumina-titania, alumina-zirconia, zinc-aluminate, alumina-boria, silica-boria, aluminophosphate-silica, titania-zirconia, and the like, or any combination thereof.

Consistent with certain aspects of this invention, the supported chromium catalyst (or the reduced chromium catalyst, or the supported chromium (II) catalyst, or the treated chromium catalyst) can comprise a chemically-treated solid oxide as the support, and where the chemically-treated solid oxide comprises a solid oxide (any solid oxide disclosed herein) treated with an electron-withdrawing anion (any electron withdrawing anion disclosed herein). The electron-withdrawing component used to treat the solid oxide can be any component that increases the Lewis or Brønsted acidity of the solid oxide upon treatment (as compared to the solid oxide that is not treated with at least one electron-withdrawing anion). According to one aspect, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phosphotungstate, tungstate, molybdate, and the like, including mixtures and combinations thereof. In addition, other ionic or non-ionic compounds that serve as sources for these electron-withdrawing anions also can be employed.

It is contemplated that the electron-withdrawing anion can be, or can comprise, fluoride, chloride, bromide, phosphate, triflate, bisulfate, or sulfate, and the like, or any combination thereof, in some aspects provided herein. In other aspects, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, and the like, or combinations thereof. Yet, in other aspects, the electron-withdrawing anion can comprise fluoride and/or sulfate.

The chemically-treated solid oxide generally can contain from 1 wt. % to 30 wt. % of the electron-withdrawing anion, based on the weight of the chemically-treated solid oxide. In particular aspects provided herein, the chemically-treated solid oxide can contain from 1 to 20 wt. %, from 2 wt. % to 20 wt. %, from 3 wt. % to 20 wt. %, from 2 wt. % to 15 wt. %, from 1 wt. % to 10 wt. %, from 2 wt. % to 10 wt. %, from 3 wt. % to 10 wt. %, of the electron-withdrawing anion, based on the total weight of the chemically-treated solid oxide.

In an aspect, the chemically-treated solid oxide can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, and the like, as well as any mixture or combination thereof.

In another aspect, the chemically-treated solid oxide employed in the supported chromium catalyst (or the reduced chromium catalyst, or the supported chromium (II) catalyst, or the treated chromium catalyst) and the processes described herein can be, or can comprise, a fluorided solid oxide and/or a sulfated solid oxide, non-limiting examples of which can include fluorided alumina, sulfated alumina, fluorided silica-alumina, sulfated silica-alumina, fluorided silica-zirconia, fluorided silica-coated alumina, sulfated silica-coated alumina, and the like, as well as combinations thereof. Additional information on chemically-treated solid oxide can be found in, for instance, U.S. Pat. Nos. 7,294,599, 7,601,665, 7,884,163, 8,309,485, 8,623,973, and 8,703,886, which are incorporated herein by reference in their entirety.

Representative examples of supported chromium catalysts, reduced chromium catalysts, supported chromium (II) catalysts, and treated chromium catalysts (in which a solid oxide is the support) include, but are not limited to, chromium/silica, chromium/silica-titania, chromium/silica-zirconia, chromium/silica-titania-magnesia, chromium/silica-alumina, chromium/silica-coated alumina, chromium/aluminophosphate, chromium/alumina, chromium/alumina borate, and the like, or any combination thereof. In one aspect, for instance, the supported chromium catalyst (or the reduced chromium catalyst, or the supported chromium (II) catalyst, or the treated chromium catalyst) can comprise chromium/silica, while in another aspect, the supported chromium catalyst (or the reduced chromium catalyst, or the supported chromium (II) catalyst, or the treated chromium catalyst) can comprise chromium/silica-titania, and in yet another aspect, the supported chromium catalyst (or the reduced chromium catalyst, or the supported chromium (II) catalyst, or the treated chromium catalyst) can comprise chromium/silica-alumina and/or chromium/silica-coated alumina. In circumstances in which the supported chromium catalyst (or the reduced chromium catalyst, or the supported chromium (II) catalyst, or the treated chromium catalyst) comprises chromium/silica-titania (or chromium/silica-zirconia), any suitable amount of titanium (or zirconium) can be present, including from 0.1 to 20 wt. %, from 0.5 to 15 wt. %, from 1 to 10 wt. %, or from 1 to 6 wt. % titanium (or zirconium), based on the total weight of the respective catalyst.

Representative examples of supported chromium catalysts, reduced chromium catalysts, supported chromium (II) catalysts, and treated chromium catalyst catalysts (in which a chemically-treated solid oxide is the support) include, but are not limited to, chromium/sulfated alumina, chromium/fluorided alumina, chromium/fluorided silica-alumina, chromium/fluorided silica-coated alumina, and the like, as well as combinations thereof.

Consistent with certain aspects of this invention, the supported chromium catalyst (or the reduced chromium catalyst, or the supported chromium (II) catalyst, or the treated chromium catalyst) can comprise a zeolite as the support, i.e., a chromium supported zeolite. Any suitable zeolite can be used, for instance, large pore and medium pore zeolites. Large pore zeolites often have average pore diameters in a range of from about 7 Å to about 12 Å, and non-limiting examples of large pore zeolites include L-zeolite, Y-zeolite, mordenite, omega zeolite, beta zeolite, and the like. Medium pore zeolites often have average pore diameters in a range of from about 5 Å to about 7 Å. Combinations of zeolitic supports can be used.

Additional representative examples of zeolites that can be used include, for instance, a ZSM-5 zeolite, a ZSM-11 zeolite, an EU-1 zeolite, a ZSM-23 zeolite, a ZSM-57 zeolite, an ALPO4-11 zeolite, an ALPO4-41 zeolite, a Ferrierite framework type zeolite, and the like, or any combination thereof.

In the supported chromium catalyst (or the reduced chromium catalyst, or the supported chromium (II) catalyst, or the treated chromium catalyst), the zeolite can be bound with a support matrix (or binder), non-limiting examples of which can include silica, alumina, magnesia, boria, titania, zirconia, various clays, and the like, including mixed oxides thereof, as well as mixtures thereof. For example, the supported chromium catalyst (or the reduced chromium catalyst, or the supported chromium (II) catalyst, or the treated chromium catalyst) can comprise a binder comprising alumina, silica, a mixed oxide thereof, or a mixture thereof. The zeolite can be bound with the binder using any method known in the art. While not being limited thereto, the supported chromium catalyst (or the reduced chromium catalyst, or the supported chromium (II) catalyst, or the treated chromium catalyst) can comprise a zeolite and from 3 wt. % to 35 wt. % binder; alternatively, from 5 wt. % to 30 wt. % binder; or alternatively, from 10 wt. % to 30 wt. % binder. These weight percentages are based on the total weight of the respective catalyst.

It is worth noting that chromium polymerization catalysts usually require chromium loadings in a rather narrow range, typically from 0.5 to 2 wt. %, because higher amounts degrade the polymer and lower amounts result in low activity. However, no such limitation exists in the present invention. Thus, the amount of chromium in the supported chromium catalyst (or the reduced chromium catalyst, or the supported chromium (II) catalyst, or the treated chromium catalyst) typically can range from 0.01 to 50 wt. %; alternatively, from 0.01 to 20 wt. %; alternatively, from 0.01 to 10 wt. %; alternatively, from 0.05 to 15 wt. %; alternatively, from 0.1 to 15 wt. %; alternatively, from 0.2 to 10 wt. %; alternatively, from 0.1 to 5 wt. %; alternatively, from 0.5 to 30 wt. %; or alternatively, from 0.5 to 2.5 wt. %. These weight percentages are based on the amount of chromium relative to the total weight of the respective catalyst. While not wishing to be bound by theory, it is believed that lower chromium loadings (e.g., 1 wt. % and less) can result in higher selectivity to a particular alcohol compound (or carbonyl compound), while higher chromium loadings (e.g., 5-15 wt. % and above) can result in higher alcohol and/or carbonyl yields per gram of catalyst.

Likewise, the reduced chromium catalyst (in step (i) of the first process and/or in step (I) of the second process), and which has an average oxidation state of +5 or less, is not particularly limited in the amount of chromium it contains, and it can fall within the same ranges. Thus, the reduced chromium catalyst can contain from 0.01 to 50 wt. %, from 0.01 to 20 wt. %, from 0.01 to 10 wt. %, from 0.05 to 15 wt. %, from 0.1 to 15 wt. %, from 0.2 to 10 wt. %, from 0.1 to 5 wt. %, from 0.5 to 30 wt. %, or from 0.5 to 2.5 wt. % of chromium in an average oxidation state of +5 or less, based on the total weight of the reduced chromium catalyst.

Generally, at least 10 wt. % of the chromium in the supported chromium catalyst (in step (i) of the first process and/or in step (I) of the second process) is present in a hexavalent oxidation state before the reduction step, and more often at least 20 wt. % is present as chromium (VI). In further aspects, at least 40 wt. %, at least 60 wt. %, at least 80 wt. %, at least 90 wt. %, or at least 95 wt. %, of the chromium in the supported chromium catalyst can be present in an oxidation state of +6. These weight percentages are based on the total amount of chromium. Traditional chromium (VI) catalysts often will have an orange, yellow, or tan color, indicating the presence of chromium (VI).

Conversely, less than or equal to 70 wt. % of the chromium in the hydrocarbon-reduced chromium catalyst is typically present in an oxidation state of +6 (VI), and more often, less than or equal to 50 wt. %, or less than or equal to 40 wt. %. In further aspects, less than or equal to 30 wt. %, or less than or equal to 15 wt. % of chromium in the reduced chromium catalyst can be present in an oxidation state of +6. The minimum amount of chromium (VI) often can be 0 wt. % (no measurable amount), at least 0.5 wt. %, at least 1 wt. %, at least 2 wt. %, or at least 5 wt. %. These weight percentages are based on the total amount of chromium. The reduced chromium catalysts often will have a green, blue, gray, or black color.

Thus, the irradiation or contacting of the supported chromium catalyst with the hydrocarbon reactant—ordinarily results in at least 10 wt. %, at least 20 wt. %, at least 40 wt. %, at least 60 wt. %, at least 80 wt. %, or at least 90 wt. %, of the supported chromium catalyst being reduced or converted to form the reduced chromium catalyst in step (i) of the first process and/or in step (I) of the second process.

Additionally or alternatively, the chromium in the hydrocarbon reduced chromium catalyst (in step (i) of the first process and/or in step (I) of the second process) can be characterized by an average valence of less than or equal to 5.25. More often, the chromium in the reduced chromium catalyst has an average valence of less than or equal to 5; alternatively, an average valence of less than or equal to 4.75; alternatively, an average valence of less than or equal to 4.5; alternatively, an average valence of less than or equal to 4.25; or alternatively, an average valence of less than or equal to 4. When the oxygen is added after reduction (sequentially) or during reduction, these valences may not be reached due to the presence of oxygen. Average valence can be determined using the procedure described in U.S. Patent Publication No. 2020/0086307.

In the third process, the supported chromium (II) catalyst in step (a) can contain any suitable amount of chromium (II), such as the ranges for chromium disclosed herein. Thus, the supported chromium (II) catalyst can contain from 0.01 to 50 wt. %, from 0.01 to 20 wt. %, from 0.01 to 10 wt. %, from 0.05 to 15 wt. %, from 0.1 to 15 wt. %, from 0.2 to 10 wt. %, from 0.1 to 5 wt. %, from 0.5 to 30 wt. %, or from 0.5 to 2.5 wt. % of chromium (II), based on the weight of the supported chromium (II) catalyst.

Generally, at least 10 wt. % of the chromium in the supported chromium (II) catalyst (in step (a) of the third process) is present in a chromium (II) before contacting the hydrocarbon reactant, and more often at least 20 wt. % is present as chromium (II). In further aspects, at least 40 wt. %, at least 50 wt. %, at least 75 wt. %, at least 85 wt. %, at least 90 wt. %, or at least 95 wt. %, of the chromium in the supported chromium (II) catalyst can be present as chromium (II).

Conversely, less than or equal to 50 wt. % of the chromium in the supported chromium (II) catalyst is typically present in an oxidation state of +6 (VI), and more often less than or equal to 35 wt. %. In further aspects, less than or equal to 20 wt. %, or less than or equal to 10 wt. % of chromium in the supported chromium (II) catalyst can be present in an oxidation state of +6. Generally, if a chromium catalyst has been reduced effectively, there will be no chromium (VI), or substantially none. Thus, the minimum amount of chromium (VI) often can be 0 wt. % (no measurable amount), at least 0.5 wt. %, at least 1 wt. %, at least 2 wt. %, or at least 5 wt. %. These weight percentages are based on the total amount of chromium.

Additionally or alternatively, the chromium in the supported chromium (II) catalyst in step (a) prior to contacting the hydrocarbon reactant can be characterized by an average valence of less than or equal to 3.5. More often, the chromium in the supported chromium (II) catalyst has an average valence of less than or equal to 3.25; alternatively, an average valence of less than or equal to 3; alternatively, an average valence of less than or equal to 2.5; or alternatively, an average valence of less than or equal to 2.25.

It is important to note that chromium polymerization catalysts require supports of high porosity so as to allow fragmentation of the catalyst and subsequent egress of the polymer chains, which are hundreds of times longer than the pore diameter in the catalyst. However, in the present invention, no such restriction exists. Thus, the total pore volume of the supported chromium catalyst (or the reduced chromium catalyst, or the supported chromium (II) catalyst, or the treated chromium catalyst) is not particularly limited. For instance, the supported chromium catalyst (or the reduced chromium catalyst, or the supported chromium (II) catalyst, or the treated chromium catalyst) can have a total pore volume in a range from 0.1 to 5 mL/g, from 0.15 to 5 mL/g, from 0.1 to 3 mL/g, from 0.5 to 2.5 mL/g, from 0.15 to 2 mL/g, from 0.3 to 1.5 mL/g, or from 0.5 to 1.0 mL/g. Likewise, the surface area of the supported chromium catalyst (or the reduced chromium catalyst, or the supported chromium (II) catalyst, or the treated chromium catalyst) is not limited to any particular range. Generally, however, the supported chromium catalyst (or the reduced chromium catalyst, or the supported chromium (II) catalyst, or the treated chromium catalyst) can have a BET surface area in a range from 50 to 2000 $m^2/g$, from 50 to 700 $m^2/g$, from 50 to 400 $m^2/g$, from 100 to 1200 $m^2/g$, from 150 to 525 $m^2/g$, or from 200 to 400 $m^2/g$.

The supported chromium catalyst (or the reduced chromium catalyst, or the supported chromium (II) catalyst, or the treated chromium catalyst) can have any suitable shape or form, and such can depend on the type of process that is employed to convert the hydrocarbon reactant into the alcohol compound and/or carbonyl compound (e.g., fixed bed versus fluidized bed). Illustrative and non-limiting shapes and forms include powder, round or spherical (e.g., a sphere), ellipsoidal, pellet, bead, cylinder, granule (e.g., regular and/or irregular), trilobe, quadrilobe, ring, wagon wheel, monolith, and the like, as well as any combination thereof. Accordingly, various methods can be utilized to prepare the supported chromium catalyst particles, including, for example, extrusion, spray drying, pelletizing, marumerizing, spheroidizing, agglomeration, oil drop, and the like, as well as combinations thereof.

In some aspects, the supported chromium catalyst (or the reduced chromium catalyst, or the supported chromium (II) catalyst, or the treated chromium catalyst) has a relatively small particle size, in which representative ranges for the average (d50) particle size of the catalyst can include from 10 to 500 microns, from 25 to 250 microns, from 20 to 100 microns, from 40 to 160 microns, or from 40 to 120 microns.

In other aspects, the supported chromium catalyst (or the reduced chromium catalyst, or the supported chromium (II)

catalyst, or the treated chromium catalyst) can be in the form of pellets or beads—and the like—having an average size ranging from 1/16 inch to 1/2 inch, or from 1/8 inch to 1/4 inch. As noted above, the size of the catalyst particles can be varied to suit the particular process for converting the hydrocarbon reactant into the alcohol compound and/or carbonyl compound.

Chromium Complexes and Oligomer Compositions

In an aspect of this invention, a supported chromium complex—and a catalyst composition comprising a supported chromium complex—having formula (A) is provided. Formula (A) is the following:

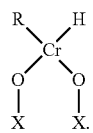
(A)

In formula (A), each X independently can be Si, Ti, Al, P, B, or Zr, and R can be a $C_1$ to $C_{36}$ hydrocarbyl group. The structure of formula (A) can result from the third process described herein, which uses a supported chromium (II) catalyst, prior to the hydrolyzing step. The supported chromium complex of formula (A) is attached to a support, as shown the by the two "X" elements. For instance, if the support is a solid oxide such as silica, then X is Si; if the support is alumina, then X is Al; if the support is titania, then X is Ti; and so forth. The X can be the same or different, if the support is a mixed oxide for instance. If the support is silica-alumina, then each X independently is Si or Al; if the support is silica-titania, then each X independently is Si or Ti; and so forth.

The $C_1$ to $C_{36}$ hydrocarbyl group can be a hydrocarbyl analog of any of the hydrocarbon reactants disclosed herein, and any range of carbon numbers, such as a $C_1$ to $C_{18}$, a $C_1$ to $C_{12}$, or a $C_1$ to $C_8$ hydrocarbyl group. Representative hydrocarbon reactants provided herein include alkane compounds, aromatic compounds, and olefin compounds; therefore, R in formula (A) can be a $C_1$ to $C_{36}$ alkyl group (alternatively, a $C_1$ to $C_{18}$ alkyl group; alternatively, a $C_1$ to $C_{12}$ alkyl group; or alternatively, a $C_1$ to $C_8$ alkyl group), a $C_6$ to $C_{36}$ aromatic group (alternatively, a $C_6$ to $C_{18}$ aromatic group; alternatively, a $C_6$ to $C_{12}$ aromatic group; or alternatively, a $C_6$ to $C_8$ aromatic group), or a $C_2$ to $C_{36}$ alkenyl group (alternatively, a $C_2$ to $C_{18}$ alkenyl group; alternatively, a $C_2$ to $C_{12}$ alkenyl group; or alternatively, a $C_2$ to $C_8$ alkenyl group). In one aspect, R can be a saturated or an unsaturated, linear or branched, aliphatic hydrocarbyl group, while in another aspect, R can be an aromatic hydrocarbyl group, and in another aspect, R can be a benzyl, tolyl, or xylyl group, and in yet another aspect, R can be a linear, branched, or cyclic alkyl group, and in still another aspect, R can be a linear, branched, or cyclic alkylene group.

Illustrative examples of R groups in formula (A) can include, but are not limited to, a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group. In some aspects, R can be a methyl group, an ethyl group, a propyl group, a butyl group, a pentyl group, or a hexyl group, while in other aspects, R can be a methyl group; alternatively, an ethyl group; alternatively, a propyl group; alternatively, a butyl group; alternatively, a pentyl group; or alternatively, a hexyl group.

Another aspect of this invention is directed to a supported chromium complex—and a catalyst composition comprising a supported chromium complex—having formula (B). Formula (B) is the following:

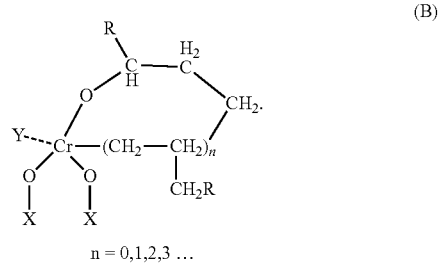
$n = 0,1,2,3 \ldots$

In formula (B), each X independently can be Si, Ti, Al, P, B, or Zr, similar to formula (A) described above. R in formula (B) can be H a $C_1$ to $C_{36}$ hydrocarbyl group (e.g., a $C_1$ to $C_{18}$, a $C_1$ to $C_{12}$, or a $C_1$ to $C_8$ hydrocarbyl group), and the hydrocarbyl group in formula (B) can be any R group described above in relation to formula (A). In formula (B), Y can be nothing (not present), $H_2O$, a $C_1$ to $C_{36}$ alcohol group (or a $C_1$ to $C_{18}$, a $C_1$ to $C_{12}$, or a $C_1$ to $C_8$ alcohol group), or a $C_2$ to $C_{36}$ ketone group (or a $C_2$ to $C_{18}$, a $C_2$ to $C_{12}$, or a $C_2$ to $C_8$ ketone group). In formula (B), n can be an integer from 0 to 10 (inclusive), for instance, n can be from 0 to 6, or n can be from 1 to 8.

The structure of formula (B) can result from any of the first process, second process, and third process described herein, in which the hydrocarbon reactant is an olefin (such as 1-pentene or 1-hexene), prior to the hydrolyzing step. After hydrolyzing, oxygenated oligomers, such as dimers and trimers, can be formed.

Another aspect of this invention is directed to a supported chromium complex—and a catalyst composition comprising a supported chromium complex—having formula (C). Formula (C) is the following:

(C)

In formula (C), each X independently can be Si, Ti, Al, P, B, or Zr, similar to formula (A) described above. Likewise, R in formula (C) can be a $C_1$ to $C_{36}$ hydrocarbyl group (e.g., a $C_1$ to $C_{18}$, a $C_1$ to $C_{12}$, or a $C_1$ to $C_8$ hydrocarbyl group), and the hydrocarbyl group in formula (C) can be any R group described above in relation to formula (A). In formula (C), Y can be —OR, —R, a $C_1$ to $C_{36}$ alcohol group (or a $C_1$ to $C_{18}$, a $C_1$ to $C_{12}$, or a $C_1$ to $C_8$ alcohol group), or a $C_2$ to $C_{36}$ ketone group (or a $C_2$ to $C_{18}$, a $C_2$ to $C_{12}$, or a $C_2$ to $C_8$ ketone group)—and R can be any $C_1$ to $C_{36}$, $C_1$ to $C_{18}$, $C_1$ to $C_{12}$, or $C_1$ to $C_8$ hydrocarbyl group disclosed herein. The structure of formula (C) can result from the third process described herein, which uses a supported chromium (II) catalyst, prior to the hydrolyzing step.

Another aspect of this invention is directed to a supported chromium complex—and a catalyst composition comprising a supported chromium complex—having formula (D). Formula (D) is the following:

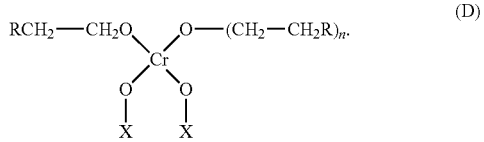

In formula (D), each X independently can be Si, Ti, Al, P, B, or Zr, similar to formula (A) described above. Likewise, R in formula (D) can be H or a $C_1$ to $C_{36}$ hydrocarbyl group (e.g., a $C_1$ to $C_{18}$, a $C_1$ to $C_{12}$, or a $C_1$ to $C_8$ hydrocarbyl group), and the hydrocarbyl group in formula (D) can be any R group described above in relation to formula (A). The integer n can range from 0 to 10 (inclusive), for instance, n can be from 0 to 6, or n can be from 1 to 8. The structure of formula (D) can result from the third process described herein, which uses a supported chromium (II) catalyst, when the hydrocarbon reactant is an olefin, and prior to the hydrolyzing step.

Other aspects of this invention are directed to compositions, such as oxygenated oligomer compositions, comprising a compound having formula (IIa) and/or formula (IIb):

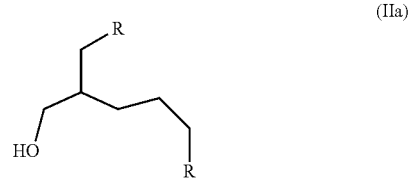

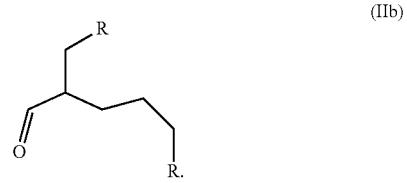

In these formulas, R can be H, a $C_6$ to $C_{18}$ aromatic group (e.g., phenyl, benzyl, and the like), or a $C_1$ to $C_{18}$ alkyl group (or a $C_1$ to $C_{12}$, a $C_1$ to $C_8$, or a $C_1$ to $C_5$ alkyl group). While not wishing to be bound by theory, it is believed that the compounds of formula (IIa) and formula (IIb) can only be produced if an oxidizing atmosphere is present as described herein in the third process, and the hydrocarbon reactant is an olefin, such as an α-olefin.

Further, the oxygenated oligomer composition can also comprise a compound having formula (IIIa) and/or formula (IIIb):

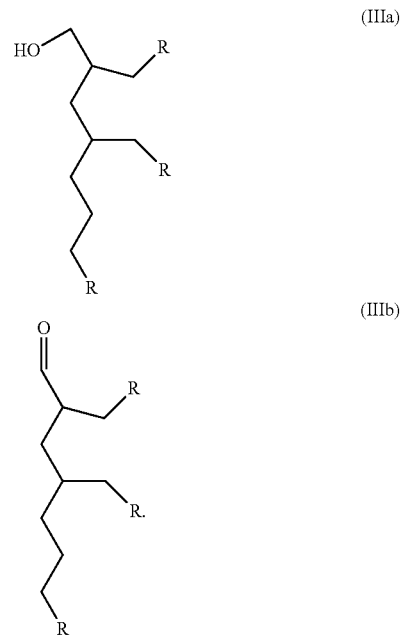

The same selections apply for formulas (IIIa) and (IIIb) as for formula (IIa) and formula (IIb). In an aspect, the R group in formulas (IIa), (IIb), (IIIa), and (IIIb) can be a linear alkyl group, while in another aspect, R can be a branched alkyl group. In yet another aspect, the R group in formulas (IIa), (IIb), (IIIa), and (IIIb) can be a hydrogen atom, a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group. In still another aspect, R can be a methyl group, an ethyl group, a propyl group, a butyl group, a pentyl group, or a hexyl group.

Another aspect of this invention is directed to a composition, such as an oxygenated oligomer composition derived from cyclohexene, comprising at least two of the following compounds: 2-cyclohexen-1,4-diol, 2-cyclohexyl cyclohexanone, 1-cyclohexyl cyclohexene, $C_{12}H_{20}O$, (1,1-bicyclohexyl)-2-one, and/or 2-cyclohexyl cyclohexanone. Similarly, another aspect of this invention is directed to a composition, such as an oxygenated oligomer composition derived from cyclopentene, comprising at least two of the following compounds: 3-cyclopentyl cyclopentene, 2-cyclopentyl cyclopentanone, and/or 2-cyclopentylidene cyclopentanone.

Examples

The invention is further illustrated by the following examples, which are not to be construed in any way as imposing limitations to the scope of this invention. Various other aspects, modifications, and equivalents thereof, which after reading the description herein, can suggest themselves to one of ordinary skill in the art without departing from the spirit of the present invention or the scope of the appended claims.

Catalyst A was a Cr/silica-titania catalyst containing 1 wt. % Cr and 4.2 wt. % Ti, with a BET surface area of 500 m²/g, a pore volume of 2.5 mL/g, and an average particle size of 130 µm. Prior to use, the catalyst was calcined in air at 800-850° C. for 3 hr to form the chromium (VI)/silica-titania catalyst containing ~1 wt. % hexavalent Cr.

Catalyst B was a Cr/silica-titania catalyst containing 1 wt. % Cr and 2.5 wt. % Ti, with a BET surface area of 500 m$^2$/g, a pore volume of 2.5 mL/g, and an average particle size of 130 µm. Prior to use, the catalyst was calcined in air at 870° C. for 3 hr to form the chromium (VI)/silica-titania catalyst containing ~1 wt. % hexavalent Cr.

Catalyst C was prepared from Catalyst A by exposing the chromium (VI)/silica-titania catalyst containing ~1 wt. % hexavalent Cr to carbon monoxide (CO) at 350° C. for 3 hr to form the chromium (II)/silica-titania catalyst containing ~1 wt. % chromium (II).

BET surface areas can be determined using the BET nitrogen adsorption method of Brunauer et al., *J. Am. Chem. Soc.*, 60, 309 (1938) as described in ASTM D1993-91. Total pore volumes can be determined in accordance with Halsey, G. D., *J. Chem. Phys.* (1948), 16, pp. 931. The d50 particle size, or median or average particle size, refers to the particle size for which 50% of the sample by volume has a smaller size and 50% of the sample has a larger size, and can be determined using laser diffraction in accordance with ISO 13320.

Table I summarizes the reactions of Examples 1-81, in which the supported chromium (VI) catalyst or the supported chromium (II) catalyst was first charged to an air-tight 100-mL glass container at 25° C. (or a different temperature if specified), followed by the addition of the hydrocarbon reactant. The glass container was then exposed to a light source as noted in Table I (note that some examples were not exposed to a light source). For all examples where the glass container was exposed to light, the container was slowly rotated at 5-10 rpm to turn over the catalyst particles in the bottle to ensure even exposure of the mixture of the catalyst and the hydrocarbon reactant to each other and to the light. For examples where the glass container was exposed to light, the sample was placed in a box containing an artificial light source (as identified in Table I), where three 15 watt bulbs were placed in a plane about 3 inches apart and about 2 inches from the bottle. Reduction of the supported chromium (VI) catalysts was monitored by the presence of a color change. Each supported chromium catalyst comprising chromium in the hexavalent oxidation state had an orange color which darkened significantly during reduction and/or upon exposing the supported chromium catalyst to light in the presence of the hydrocarbon reactant, and usually assuming a green or blue color, indicating reduction of the supported chromium catalyst starting material, and formation of the reduced chromium catalyst.

The light sources used in Table I were white fluorescent (440-640 nm) and blue fluorescent (425-475 nm) at a lux of ~54,000-73,000, and blue LED (400-450 nm) and UV LED (380-405 nm) at a lux of ~75,000-80,000.

In some examples, an oxidizing atmosphere was provided by adding dry air (1 atm) to the 100-mL glass container, either "during" the reduction (while the catalyst and the hydrocarbon reactant were being contacting, and in some examples while being irradiated) or at the "end" of the reduction (after contacting and/or irradiating, but before hydrolysis). This was accomplished by injecting a stream of dry air into the container over about 30 seconds, which usually resulted in an immediate color change. Total exposure time to the air, prior to hydrolysis, was approximately 1 minute.

After the desired contact time or exposure time, the reduced chromium catalyst or the treated chromium catalyst was mixed with a hydrolysis agent to cleave the hydrocarbon-containing ligand(s) from the chromium catalyst. The mixture was stirred for several minutes. The hydrolysis agent used was generally selected so as to not interfere with analysis of the reaction product (e.g., methanol was not used as the hydrolysis agent when the reaction product after hydrolysis could contain methanol, etc.).

Table I summarizes the results of Examples 1-81, and lists the catalyst type, catalyst and amount, the hydrocarbon reactant and amount, the light treatment, the air treatment, the hydrolysis agent and amount, the acid or base used in hydrolysis, the total products analyzed/Cr (molar), and an analysis of the reaction product (oxygenated products) after hydrolysis. The reaction product analysis includes only oxygen-containing products that were derivable from the reductant/reactant and does not include, for example, materials resulting from the hydrolysis agent or its by-products, or oligomers resulting from polymerization. For the oxygenated reaction products, area % from the analytical procedures listed below is roughly equivalent to mol %, thus the results in Table I are shown in mol %.

When ethylene was the hydrocarbon reactant, carboxylic acid products were determined by first neutralizing the product acids with a solution of sodium hydroxide to put them into the ionic form. Then, a small amount of the sample was injected through an ion column designed to separate anions from weak organic acids through an ion chromatography process. A Dionex® IC-3000 instrument with an ICE-AS1 column and guard was used. The test was specifically sensitive to linear carboxylic acids from $C_1$ to $C_6$, glutarate and glycolate ions. Results were reported in micrograms of carboxylate per mL of solution, which was then converted to moles.

When ethylene was the hydrocarbon reactant, lower alcohol products were determined using a GC-MS procedure, with an Agilent® 6890 gas chromatograph having a flame-ionizing detector (FID). It used a Restek® Stapilwax column (P/N 10658) designed and gated specifically to separate and detect light alcohols. The procedure was gated for acetone, methanol, ethanol, isopropanol, n-propanol, isobutanol, n-butanol, t-butanol, 2-butanol, 2-butoxyethanol, acetonitrile and tetrahydrofuran.

For all hydrocarbon reactants, the redox reaction products (and Redox Products/Cr on a molar basis, except for ethylene) were determined using another GC-MS procedure, as follows. Gas chromatography was performed using an Agilent® 7890B GC equipped with both flame ionizing and mass spectral analysis. An all-purpose capillary column (Agilent® J&W® VF-5 ms, 30 m×0.25 mm×0.25 µm) was used with variable temperature. Approximate 0.5 µL sample aliquots were injected into a GC port held at 250° C. using a split ratio of 10:1. The carrier gas was ultra-high purity helium and was electronically controlled throughout the run to a constant flow rate of 1.2 mL/min. Initial column temperature was held at 50° C. for 5 min, ramped at 20° C./min to 250° C., and then held at 250° C. for 19 min. Spectral assignment was made via mass correlation using an Agilent® 5977B mass spectrometer connected to the GC unit using electron ionization at 70 eV. The nominal mass range scanned was 14-400 m/z using a scan time of 0.5 sec. Nominal detector voltage used was 1200 V. For calibration purposes both the FID and MS detectors were sometimes used in sequence on the same or reference samples.

Due to the wide range of oxygenated products produced herein, one or all of these three procedures were used to characterize the reaction product after hydrolysis. In some cases, the same compound was detected by more than one technique, and this was subtracted out of the total/Cr (on a molar basis) to prevent double counting of the same compound by more than one analytical technique. For the most part, however, there was very little overlap between the three analytical procedures.

Referring now to the data in Table I, Examples 1-19 demonstrate the conversion of alkanes (n-pentane, isopentane, cyclopentane, cyclohexane, and isobutane) and aromatics (benzene and toluene) into analogous alcohol and carbonyl products at ambient temperature (or −78° C.) using Catalyst A or Catalyst B under a variety of irradiation treatments, oxygen exposures, and hydrolysis agents. In all cases where oxygen was present during reduction or oxygen was present at the end of the reduction (but prior to hydrolysis), there was an unexpected and significant increase in the yield of the oxygenated products, as quantified by redox products/chromium on a molar basis. In some examples, the molar amount of redox products/chromium on a molar basis was over 1, such as 1.3-1.6.

Examples 20-48 demonstrate the conversion of olefins (ethylene, 1-pentene, 2-pentene, cyclopentene, 1-hexene, and cyclohexene) into analogous alcohol and carbonyl products at ambient temperature (or −78° C.) using Catalyst A or Catalyst B under a variety of irradiation treatments, oxygen exposures, and hydrolysis agents. Generally, where oxygen was present during reduction or oxygen was present at the end of the reduction (but prior to hydrolysis), there was an unexpected and significant increase in the yield of the oxygenated products, as quantified by redox products/chromium on a molar basis. In some examples, the molar amount of redox products/chromium on a molar basis was over 1, such as 1.4 up to and including 2.5-5.4.

Referring now to Examples 49-71 in Table I, these examples demonstrate the conversion of alkanes (cyclohexane, n-pentane, n-hexane, cyclopentane, and isopentane) and aromatics (benzene, toluene, and ethylbenzene) into analogous alcohol and carbonyl products at ambient temperature using Catalyst C—a chromium (II) catalyst—under a variety of irradiation treatments, oxygen exposures, and hydrolysis agents. Light treatment was not required for chromium (II) catalysts, but it was used in some experiments, nonetheless. For examples where there was no oxygen exposure, no alcohol or carbonyl products were produced, whereas oxygen exposure at the end of the hydrocarbon treatment, with or without light exposure (but prior to hydrolysis), there was an unexpected and significant yield of the oxygenated products, as quantified by redox products/chromium on a molar basis. Generally, the molar amount of redox products/chromium on a molar basis was from 0.3 to 1.8.

Examples 72-81 demonstrate the conversion of olefins (ethylene, 1-pentene, 2-pentene, 1-hexene, and cyclohexene) into analogous alcohol and carbonyl products at ambient temperature using Catalyst C—a chromium (II) catalyst—under a variety of irradiation treatments, oxygen exposures, and hydrolysis agents. As above, for examples where there was no oxygen exposure, no alcohol or carbonyl products were produced, whereas oxygen exposure at the end of the hydrocarbon treatment, with or without light exposure (but prior to hydrolysis), there was an unexpected and significant yield of the oxygenated products, as quantified by redox products/chromium on a molar basis. Generally, the molar amount of redox products/chromium on a molar basis was from 0.3 to 2.3.

For the chromium (II) catalyst, exposure to the hydrocarbon followed by hydrolysis produced no alcohols/carbonyls, whether irradiated or not. Likewise, adding air to the chromium (II) catalyst, followed by hydrocarbon addition and hydrolysis after a few minutes, also produced no alcohols/carbonyls. Additionally, contacting the chromium (II) catalyst, air, and the hydrocarbon simultaneously, followed by hydrolysis also produced no alcohols/carbonyls.

While the focus of these examples was not to maximize chromium conversion (or yield to any particular alcohol or carbonyl compound), the total/Cr molar value in Table I illustrates that significant chromium conversion and alcohol/carbonyl yield can be achieved, depending of course on the hydrocarbon reactant, the catalyst (and chromium loading), the irradiation conditions, and the presence of oxygen, among other factors.

Table II includes numerous examples from Table I and Examples A-S, which were performed in a manner similar to the examples in Table I. Table II summarizes the hydrocarbon reactant, the catalyst type, the presence of air, and the amount of oxygenated dimers, trimers, and tetramers produced (on a molar basis per mole of chromium). In addition to the redox products—such as allylic and other alcohols—listed in Table I, a significant and unexpected amount of oxygenated oligomers were produced in many of the examples. Oxygenated dimers often were the most prevalent, and in some examples, oxygenated dimers were formed at molar amounts in excess of 5 moles of oxygenated dimer per mole of chromium. Oxygenated trimers and tetramers also were formed and could be detected in many examples, and often in significant molar amounts. In many cases, higher oligomers were present, but often were not soluble enough in the quench solution (e.g., water) and thus were not be detected by GC-MS.

TABLE I

Summary of Examples 1-81 (products in mol %)

| Examples 1-4 | 1 | Amount | 2 | Amount | 3 | Amount | 4 | Amount |
|---|---|---|---|---|---|---|---|---|
| Catalyst type | Cr(VI) | | Cr(VI) | | Cr(VI) | | Cr(VI) | |
| Catalyst/ Amount | A | 1.89 g | A | 2.04 g | A | 2.04 g | A | 1.61 g |
| Reductant | n-pentane | 2 mL | n-pentane | 2 mL | n-pentane | 1 mL | n-pentane | 1 mL |
| Light | UV | 24 h | UV | 26 h | UV | 18 h | UV | 18 h |
| Air | at end | | none | | at end | | none | |

TABLE I-continued

Summary of Examples 1-81 (products in mol %)

| Hydrolysis | 5% H₂O/MeOH | 15 mL | 5% H₂O/MeOH | 15 mL | 4% H₂O/MeOH | 15 mL | 4% H₂O/MeOH | 15 mL |
|---|---|---|---|---|---|---|---|---|
| Acid or Base | none | | none | | none | | none | |
| Redox Products/Cr | 1.400 | | 0.483 | | 1.317 | | 0.965 | |
| Products | 2&3-pentanols | 46% | 2&3-pentanols | 44% | 2&3-pentanols | 57% | 2&3-pentanols | 57% |
| | 1-pentanol | 19% | 1-pentanol | 24% | 1-pentanol | 16% | 1-pentanol | 20% |
| | 2-pentanone | 15% | 2-pentanone | 17% | 2-pentanone | 13% | 2-pentanone | 18% |
| | 3-pentanone | 10% | 3-pentanone | 11% | 3-pentanone | 8% | 3-pentanone | 6% |
| | pentanal | 6% | 3-penten-2-one | 3% | pentanal | 5% | | |
| | 3-penten-2-one | 2% | 2-pentenal | 2% | C₅H₁₀O | 2% | | |
| | 2-pentenal | 2% | | | | | | |

| Examples 5-8 | 5 | Amount | 6 | Amount | 7 | Amount | 8 | Amount |
|---|---|---|---|---|---|---|---|---|
| Catalyst type | Cr(VI) | | Cr(VI) | | Cr(VI) | | Cr(VI) | |
| Catalyst/Amount | A | 1.83 g | A | 1.24 g | A | 1.09 g | A | 2.10 g |
| Reductant | n-pentane | 2 mL | isopentane | 2 mL | isopentane | 2 mL | cyclopentane | 2 mL |
| Light | white light | | UV during reduction | 4.5 h | UV | 4.5 h | UV | 6 h |
| Air | none | | | | none | | at end | |
| Hydrolysis | 12% H₂O/MeOH | 15 mL | 5% H₂O/MeOH | 15 mL | 5% H₂O/MeOH | 15 mL | 7% H₂O/EtOH | 15 mL |
| Acid or Base | NaHSO₃ | | none | | none | | 0.1% HCl | |
| Redox Products/Cr | 0.456 | | 0.955 | | 0.570 | | 1.126 | |
| Products | 2&3-pentanols | 66% | t-pentanol | 35% | t-pentanol | 28% | cyclopentanol | 68% |
| | 1-pentanol | 22% | 2-Me-1-butanol | 23% | 2-Me-1-butanol | 30% | cyclopentanone | 15% |
| | 2-pentanone | 6% | 3-Me-2-butanol | 15% | 3-Me-2-butanol | 17% | cyclopentane oxide | 12% |
| | 3-pentanone | 3% | isoamyl alcohol | 10% | isoamyl alcohol | 15% | 2-cyclopenten-1-ol | 4% |
| | pentanal | 2% | 3-Me-2-butanone | 10% | 3-Me-2-butanone | 10% | 2-cyclopenten-1-one | 1% |
| | C₅H₁₀O | 1% | 3-Me-3-buten-2-one | 3% | | | | |
| | | | isopentanoic acid | 5% | | | | |

| Examples 9-12 | 9 | Amount | 10 | Amount | 11 | Amount | 12 | Amount |
|---|---|---|---|---|---|---|---|---|
| Catalyst type | Cr(VI) | | Cr(VI) | | Cr(VI) | | Cr(VI) | |
| Catalyst/Amount | A | 2.09 g | A | 1.81 g | A | 1.11 g | A | 0.96 g |
| Reductant | cyclopentane | 2 mL | cyclopentane | 2 mL | cyclohexane | 1 mL | cyclohexane | 1 mL |
| Light | UV | 6 h | white light | 2 h | UV | 3.8 h | UV | 3.8 h |
| Air | none | | none | | at end | | none | |
| Hydrolysis | 7% H₂O/EtOH | 15 mL | 12% H₂O/MeOH | 15 mL | 7% H₂O/EtOH | 15 mL | 7% H₂O/EtOH | 15 mL |
| Acid or Base | 0.1% HCl | | NaHSO₃ | | 0.1% HCl | | 0.1% HCl | |
| Redox Products/Cr | 0.130 | | 0.48 | | 0.222 | | 0.128 | |
| Products | cyclopentanol | 85% | cyclopentanol | 87% | cyclohexanol | 77% | cyclohexanol | 57% |
| | cyclopentanone | 15% | cyclopentanone | 13% | cyclohexene | 13% | cyclohexene | 38% |
| | | | | | cyclohexanone | 7% | cyclohexanone | 5% |
| | | | | | 2-cyclohexen-1-ol | 3% | | |

| Examples 13-16 | 13 | Amount | 14 | Amount | 15 | Amount | 16 | Amount |
|---|---|---|---|---|---|---|---|---|
| Catalyst type | Cr(VI) | | Cr(VI) | | Cr(VI) | | Cr(VI) | |
| Catalyst/Amount | B | 3.22 g | B | 1.20 g | A | 2.38 g | A | 2.06 g |
| Reductant | cyclohexane | 4 mL | cyclohexane | 4 mL | isobutane | 15 psi | benzene | 2 mL |
| Light | Blue lt., −78° C. | 18 h | Blue lt., −78° C. | 18 h | UV | 2 h | UV | 6 h |
| Air | at end | | at end | | at end | | at end | |
| Hydrolysis | 4% H₂O/MeOH | 15 mL | 4% H₂O/MeOH | 15 mL | 7% H₂O/EtOH | 15 mL | 7% H₂O/EtOH | 15 mL |

TABLE I-continued

Summary of Examples 1-81 (products in mol %)

| | | | | | | | | |
|---|---|---|---|---|---|---|---|---|
| Acid or Base | none | | none | | 0.1% HCl | | 0.1% HCl | |
| Redox Products/Cr | 1.552 | | 0.668 | | 0.336 | | 0.217 | |
| Products | cyclohexanol | 79% | cyclohexanol | 49% | t-butanol | 46% | phenol | 100% |
| | cyclohexanone | 13% | cyclohexanone | 40% | isobutanol | 39% | | |
| | cyclohexene oxide | 7% | 2-cyclohexen-1-one | 7% | 2-Me-2-propenal | 9% | | |
| | 2-cyclohexen-1-ol | 1% | cyclo-hexanediol | 2% | 2-Me-2-propen-1-ol | 6% | | |
| | | | CH$_6$H$_{10}$O$_2$ dimer | 1% | | | | |

| Examples 17-20 | 17 | Amount | 18 | Amount | 19 | Amount | 20 | Amount |
|---|---|---|---|---|---|---|---|---|
| Catalyst type | Cr(VI) | | Cr(VI) | | Cr(VI) | | Cr(VI) | |
| Catalyst/Amount | A | 1.98 g | A | 1.94 g | A | 2.02 g | A | 0.92 g |
| Reductant | benzene | 2 mL | toluene | 2 mL | toluene | 2 mL | ethylene | 1.5 psi |
| Light | UV | 6 h | UV | 6 h | UV | 6 h | UV | 4 h |
| Air | none | | at end | | none | | during reduction | |
| Hydrolysis | 7% H$_2$O/EtOH | 15 mL | 7% H$_2$O/EtOH | 15 mL | 7% H$_2$O/EtOH | 15 mL | H$_2$O | 15 mL |
| Acid or Base | 0.1% HCl | | 0.1% HCl | | 0.1% HCl | | none | |
| Redox Products/Cr | 0.057 | | 0.487 | | 0.265 | | 0.341 | |
| Products | phenol | 100% | benzaldehyde | 53% | benzaldehyde | 61% | ethanediol | 47% |
| | | | 2-Me-phenol | 13% | 2-Me-phenol | 11% | formate | 29% |
| | | | 4-Me-phenol | 9% | 4-Me-phenol | 9% | C$_6$H$_{12}$O$_2$ | 18% |
| | | | 1-Me-2-(PhMe)-benzene | 9% | 1-Me-2-(PhMe)-benzene | 7% | diethanediol | 5% |
| | | | benzyl alcohol | 5% | benzyl alcohol | 3% | acetate | 2% |
| | | | (4-methylphenyl)-phenyl-methanone | 5% | (4-methylphenyl)-phenyl-methanone | 4% | | |
| | | | 1-Me-3-(PhMe)-benzene | 4% | 1-Me-3-(PhMe)-benzene | 3% | | |
| | | | (2-methylphenyl)-phenyl-methanone | 3% | | 2% | | |

| Examples 21-24 | 21 | Amount | 22 | Amount | 23 | Amount | 24 | Amount |
|---|---|---|---|---|---|---|---|---|
| Catalyst type | Cr(VI) | | Cr(VI) | | Cr(VI) | | Cr(VI) | |
| Catalyst/Amount | A | 2.04 g | A | 2.04 g | A | 1.95 g | A | 1.87 g |
| Reductant | ethylene | 1.5 psi | ethylene | 1.5 psi | ethylene | 1.5 psi | 1-pentene | 1 psi |
| Light | UV | 24 h | UV | 5 h | UV | 4 h | UV | 18 h |
| Air | none | | during reduction | | none | | at end | |
| Hydrolysis | H$_2$O | 15 mL | 4% H$_2$O/MeOH | 15 mL | 4% H$_2$O/MeOH | 15 mL | 4% H$_2$O/MeOH | 15 mL |
| Acid or Base | none | | none | | none | | none | |
| Redox Products/Cr | 0.266 | | 0.128 | | 0.020 | | 0.296 | |
| Products | ethanediol | 53% | ethanediol | 100% | ethanediol | 100% | 1-penten-3-ol | 39% |
| | formate | 29% | formate | 0% | formate | 0% | C$_5$H$_{10}$O | 20% |
| | C$_6$H$_{12}$O$_2$ | 0% | C$_6$H$_{12}$O$_2$ | 0% | C$_6$H$_{12}$O$_2$ | 0% | 2-penten-1-ol | 14% |
| | diethanediol | 17% | diethanediol | 0% | diethanediol | 0% | pentanoic acid | 10% |
| | acetate | 1% | acetate | 0% | acetate | 0% | butanal | 9% |
| | | | | | | | C$_5$H$_{10}$O | 8% |

TABLE I-continued

Summary of Examples 1-81 (products in mol %)

| Examples 25-28 | 25 | Amount | 26 | Amount | 27 | Amount | 28 | Amount |
|---|---|---|---|---|---|---|---|---|
| Catalyst type | Cr(VI) | | Cr(VI) | | Cr(VI) | | Cr(VI) | |
| Catalyst/Amount | A | 1.91 | A | 1.93 g | A | 1.91 g | A | 2.40 g |
| Reductant | 1-pentene | 1 mL | 1-pentene | 0.5 mL | 1-pentene | 0.5 mL | 1-pentene | 0.5 mL |
| Light | UV | 18 h | no light | 3.5 h | no light | 3.5 h | none | 35 min |
| Air | none | | at end | | none | | at end | |
| Hydrolysis | 4% $H_2O$/MeOH | 15 mL | 7% $H_2O$/EtOH | 15 mL | 7% $H_2O$/EtOH | 15 mL | 7% $H_2O$/EtOH | 15 mL |
| Acid or Base | none | | 0.1% HCl | | 0.1% HCl | | 0.1% HCl | |
| Redox Products/Cr | 0.076 | | 0.093 | | 0.046 | | 0.578 | |
| Products | 1-penten-3-ol | 75% | 1-penten-3-ol | 57% | 1-penten-3-ol | 72% | 1-penten-3-ol | 25% |
| | $C_5H_{12}O$ | 25% | pentanal | 13% | 2-pentenal | 28% | $C_5H_{10}O$ | 23% |
| | | | 2-pentenal | 7% | | | 2-pentenal | 14% |
| | | | butanal | 6% | | | $C_5H_{10}O$ | 9% |
| | | | 1-pentanol | 5% | | | 2-penten-1-ol | 7% |
| | | | $C_5H_{10}O$ | 4% | | | $C_5H_{10}O$ | 5% |
| | | | $C_5H_{12}O$ | 4% | | | 3-pentanol | 3% |
| | | | 2-pentanol | 4% | | | 3-penten-1-ol | 2% |
| | | | | | | | butanal | 2% |
| | | | | | | | 4-penten-2-ol | 2% |
| | | | | | | | $C_5H_{12}O$ | 2% |

| Examples 29-32 | 29 | Amount | 30 | Amount | 31 | Amount | 32 | Amount |
|---|---|---|---|---|---|---|---|---|
| Catalyst type | Cr(VI) | | Cr(VI) | | Cr(VI) | | Cr(VI) | |
| Catalyst/Amount | A | 2.20 g | A | 1.92 g | A | 1.93 g | A | 2.05 g |
| Reductant | 1-pentene | 2 mL | 2-pentene | 2 mL | 2-pentene | 2 mL | 2-pentene | 0.5 mL |
| Light | white light | 2 h | none | 1.5 h | none | 1.5 h | none | 3.5 h |
| Air | none | | at end | | none | | at end | |
| Hydrolysis | 12% $H_2O$/MeOH | 15 mL | 7% IPA in benzene | 15 mL | 7% IPA in benzene | 15 mL | 7% $H_2O$/EtOH | 15 mL |
| Acid or Base | $NaHSO_3$ | | none | | none | | 0.1% HCl | |
| Redox Products/Cr | 0.290 | | 0.086 | | 0.077 | | 0.403 | |
| Products | 1-penten-3-ol | 34% | C5 oxygenate | 23% | pentanal | 54% | 1-penten-3-ol | 56% |
| | 3-penten-2-ol | 16% | 3-penten-2-ol | 22% | 3-penten-2-ol | 23% | 1-penten-3-one | 15% |
| | 2-pentenal | 15% | pentanal | 20% | 3-penten-2-one | 15% | 3-penten-2-ol | 5% |
| | $C_5H_{12}O$ | 7% | 3-penten-2-one | 11% | pentanediol | 8% | 3-pentanol | 4% |
| | $C_5H_{10}O$ | 7% | C5 oxygenate | 11% | | | 3-penten-2-one | 3% |
| | butanal | 5% | pentanediol | 7% | | | 4-penten-1-ol | 3% |
| | pentanal | 4% | 2-penten-1-ol | 7% | | | 1-pentanol | 3% |
| | 2-penten-1-ol | 4% | | | | | 2-pentanol | 3% |
| | 2-pentanol | 2% | | | | | 2-pentanone | 2% |
| | butanol | 2% | | | | | 4-penten-2-ol | 2% |
| | 3-pentanone | 2% | | | | | 2-penten-1-one | 2% |
| | 3-penten-2-one | 1% | | | | | 2-penten-1-ol | 1% |
| | butanol | 1% | | | | | | |

| Examples 33-36 | 33 | Amount | 34 | Amount | 35 | Amount | 36 | Amount |
|---|---|---|---|---|---|---|---|---|
| Catalyst type | Cr(VI) | | Cr(VI) | | Cr(VI) | | Cr(VI) | |
| Catalyst/Amount | A | 1.95 g | A | 2.02 g | A | 1.98 g | B | 1.02 g |
| Reductant | 2-pentene | 0.5 mL | cyclopentene | 0.5 mL | cyclopentene | 0.5 mL | 1-hexene | 2 mL |
| Light | none | 3.5 h | none | 3.5 h | none | 3.5 h | UV | 4.5 h |
| Air | none | | at end | | none | | during reduction | |
| Hydrolysis | 7% $H_2O$/EtOH | 15 mL | 7% $H_2O$/EtOH | 15 mL | 7% $H_2O$/EtOH | 15 mL | 5% $H_2O$/MeOH | 15 mL |
| Acid or Base | 0.1% HCl | | 0.1% HCl | | 0.1% HCl | | none | |
| Redox Products/Cr | 0.138 | | 0.457 | | 0.201 | | 1.384 | |
| Products | 3-penten-2-ol | 42% | cyclopentane oxide | 36% | 2-cyclopenten-1-ol | 44% | 2-hexen-1-ol | 30% |
| | 1-penten-3-ol | 29% | 2-cyclopenten- | 28% | 2-cyclopenten- | 42% | 1,2-hexanediol | 25% |

TABLE I-continued

Summary of Examples 1-81 (products in mol %)

| | | | 1-ol | | 1-one | | | |
|---|---|---|---|---|---|---|---|---|
| | 2-pentanol | 14% | 2-cyclopenten-1-one | 24% | 4-pentenal | 6% | 1-hexen-3-ol | 15% |
| | 1-penten-3-one | 7% | 1,2-cyclopentanediol | 8% | cyclopentanol | 3% | 2-hexenal | 8% |
| | 2-pentanone | 5% | pentanedial | 3% | pentanedial | 3% | 3-hexen-2-one | 5% |
| | 3-penten-2-one | 2% | cyclopentanol | 1% | 2-butanone | 1% | 2-hexanone | 5% |
| | 3-pentanol | 1% | | | | | 3-hexanol | 4% |
| | | | | | | | hexanal | 4% |
| | | | | | | | 2,3-hexanediol | 4% |

| Examples 37-40 | 37 | Amount | 38 | Amount | 39 | Amount | 40 | Amount |
|---|---|---|---|---|---|---|---|---|
| Catalyst type | Cr(VI) | | Cr(VI) | | Cr(VI) | | Cr(VI) | |
| Catalyst/Amount | B | 1.77 g | B | 1.21 g | A | 2.38 g | A | 2.24 g |
| Reductant | 1-hexene | 2 mL | 1-hexene | 2 mL | 1-hexene | 2 mL | 1-hexene | 2 mL |
| Light | UV | 24 h | UV | 4.5 h | none | 1.5 h | none | 3 h |
| Air | at end | | none | | at end | | none | |
| Hydrolysis | 5% H$_2$O/MeOH | 15 mL | 5% H$_2$O/MeOH | 15 mL | 4% H$_2$O/MeOH | 15 mL | 4% H$_2$O/MeOH | 15 mL |
| Acid or Base | none | | none | | none | | none | |
| Redox Products/Cr | 0.547 | | 0.458 | | 0.737 | | 0.594 | |
| Products | 2-hexanone | 42% | hexanal | 21% | 2-hexen-1-ol | 33% | 1-hexen-3-ol | 22% |
| | 2-hexen-1-ol | 20% | 1-hexen-3-ol | 19% | 1-hexen-3-ol | 15% | 2-hexenal | 18% |
| | 2-hexenal | 11% | 2-pentenal | 15% | 2-hexenal | 12% | C$_6$H$_{12}$O | 14% |
| | hexanal | 7% | 2-hexenal | 15% | 2-hexanone | 6% | C$_6$H$_{12}$O | 12% |
| | 1-hexanol | 7% | 3-hexanol | 13% | hexanal | 6% | C$_6$H$_{12}$O | 11% |
| | 1-hexen-3-one | 6% | 2-hexanone | 9% | 2-hexen-1-ol | 6% | C$_6$H$_{12}$O | 10% |
| | pentanal | 6% | 1,2-hexanediol | 8% | pentanal | 5% | C$_6$H$_{12}$O | 6% |
| | 3-hexen-2-one | 5% | | | 5-hexen-2-one | 5% | C$_6$H$_{10}$O | 4% |
| | 1-hexen-3-ol | 5% | | | 1-hexen-3-one | 4% | 2-hexen-1-ol | 4% |
| | 5-hexen-2-one | 4% | | | 2-pentenal | 3% | | |
| | 3-hexanone | 3% | | | 5-hexen-1-ol | 3% | | |
| | | | | | 1-hexanol | 2% | | |

| Examples 41-44 | 41 | Amount | 42 | Amount | 43 | Amount | 44 | Amount |
|---|---|---|---|---|---|---|---|---|
| Catalyst type | Cr(VI) | | Cr(VI) | | Cr(VI) | | Cr(VI) | |
| Catalyst/Amount | A | 2.61 g | A | 2.34 g | B | 3.82 g | A | 2.59 g |
| Reductant | 1-hexene | 2 mL | 1-hexene | 2 mL | cyclohexene | 1 mL | cyclohexene | 2 mL |
| Light | UV | 30 min | UV | 30 min | UV | 18 min | blue LED light-78° C. | 4 min |
| Air | at end | | none | | during reduction | | at end | |
| Hydrolysis | 4% H$_2$O/MeOH | 15 mL | 4% H$_2$O/MeOH | 15 mL | 4% H$_2$O/MeOH | 15 mL | 4% H$_2$O/MeOH | 15 mL |
| Acid or Base | none | | none | | none | | none | |
| Redox Products/Cr | 1.434 | | 0.533 | | 5.385 | | 4.574 | |
| Products | 2-hexanone | 18% | 1-hexen-3-ol | 24% | 2-cyclohexen-1-one | 39% | 2-cyclohexe-1-one | 33% |
| | 1-hexen-3-ol | 17% | 2-hexenal | 20% | 5-hexenal | 27% | 2-cyclohexe-1-ol | 23% |
| | 2-hexenal | 16% | hexanal | 12% | 2-cyclohexen-1-ol | 16% | 1,2-cyclohexanediol | 20% |
| | 2-hexen-1-ol | 15% | 2-hexanone | 11% | 1,2-cyclohexanediol | 7% | cyclohexene oxide | 13% |
| | hexanal | 6% | 5-hexen-2-one | 6% | 1,2-cyclohexanediol | 3% | cyclohexyl cyclohexanone | 5% |
| | 5-hexen-2-one | 5% | 3-hexanone | 5% | 1,2-cyclohexanediol | 3% | 1,2-cyclohexanediol | 2% |
| | 3-hexanone | 3% | 2-hexen-1-ol | 4% | 2-OH-hexanone | 2% | 1-cyclohexenol | 2% |
| | 1-hexen-3-one | 3% | 1-hexen-3-one | 4% | 1-cyclohexenol | 1% | 2-OH-cyclohexanone | 1% |
| | 3-hexen-2-one | 3% | 3-hexen-2-one | 4% | 3-cyclohexen-1-ol | 1% | cyclohexanone | 0% |
| | 2-hexen-1-ol | 3% | 2-hexen-1-ol | 4% | 2-cyclohexen-1,4-diol | 0% | hexandial | 0% |

TABLE I-continued

Summary of Examples 1-81 (products in mol %)

| Examples 45-48 | 45 | Amount | 46 | Amount | 47 | Amount | 48 | Amount |
|---|---|---|---|---|---|---|---|---|
| Catalyst type | Cr(VI) | | Cr(VI) | | Cr(VI) | | Cr(VI) | |
| Catalyst/Amount | B | 1.83 g | B | 1.80 g | A | 2.05 g | A | 1.96 g |
| Reductant | cyclohexene | 1.5 mL | cyclohexene | 1 mL | cyclohexene | 0.5 mL | cyclohexene | 0.5 mL |
| Light | none | 30 min | none | 30 min | none | 3.5 min | none | 3.5 min |
| Air | none | | during reduction | | at end | | none | |
| Hydrolysis | 4% $H_2O$/MeOH | 15 mL | 4% $H_2O$/MeOH | 15 mL | 7% $H_2O$/EtOH | 15 mL | 7% $H_2O$/EtOH | 15 mL |
| Acid or Base | none | | none | | 0.1% HCl | | 0.1% HCl | |
| Redox Products/Cr | 0.695 | | 2.593 | | 0.713 | | 0.185 | |
| Products | 2-cyclohexen-1-ol | 49% | 4-Me-2-pentanone | 32% | 2-cyclohexen-1-ol | 42% | 2-cyclohexen-1-ol | 46% |
| | 2-cyclohexen-1-one | 38% | 2-cyclohexene-1-ol | 19% | 2-cyclohexen-1-one | 31% | 2-cyclohexen-1-one | 38% |
| | cyclohexyl cyclohexanol | 7% | 1,2-cyclohexanediol | 19% | 1-cyclohexenol | 12% | $C_{12}H_{22}O_2$ | 4% |
| | 2-cyclohexyl cyclohexanone | 4% | 2-cyclohexene-1-one | 18% | 1,2-cyclohexanediol | 6% | 2-cyclohexyl cyclohexanone | 6% |
| | cyclohexene oxide | 2% | 1,3-cyclohexanediol | 3% | C12 oxygenate | 3% | C12 oxygenate | 1% |
| | | | cyclohexene oxide | 2% | 2-cyclohexyl cyclohexanone | 3% | C12 oxygenate | 6% |
| | | | 2-cyclohexene-1,4-diol | 2% | $C_{12}H_{20}O_2$ | 2% | | |
| | | | cyclohexyl cyclohexanone | 1% | $C_{12}H_{20}O_2$ | 2% | | |

| Examples 49-52 | 49 | Amount | 50 | Amount | 51 | Amount | 52 | Amount |
|---|---|---|---|---|---|---|---|---|
| Catalyst type | Cr(II) | | Cr(II) | | Cr(II) | | Cr(II) | |
| Catalyst/Amount | C | 2.43 g | C | 2.14 g | C | 4.09 g | C | 2.55 g |
| Reductant | cyclohexane | 2 mL | cyclohexane | 2 mL | cyclohexane | 2 mL | cyclohexane | 2 mL |
| Light | UV | 70 min | UV | 70 min | none | 2.5 h | none | 2.5 h |
| Air | at end | | none | | at end | | none | |
| Hydrolysis | 5% $H_2O$/MeOH | 15 mL | 5% $H_2O$/MeOH | 15 mL | 4% $H_2O$/MeOH | 15 mL | 4% $H_2O$/MeOH | 15 mL |
| Acid or Base | None. | | none | | none | | none | |
| Redox Products/Cr | 1.745 | | 0 | | 0.986 | | 0 | |
| Products | cyclohexanol | 68% | none | | cyclohexanol | 84% | none | |
| | 2-cyclohexen-1-one | 16% | | | cyclohexanone | 7% | | |
| | cyclohexanone | 13% | | | cyclohexene oxide | 5% | | |
| | cyclohexene oxide | 3% | | | cyclohexene | 4% | | |

| Examples 53-56 | 53 | Amount | 54 | Amount | 55 | Amount | 56 | Amount |
|---|---|---|---|---|---|---|---|---|
| Catalyst type | Cr(II) | | Cr(II) | | Cr(II) | | Cr(II) | |
| Catalyst/Amount | C | 2.04 g | C | 1.88 g | C | 2.36 g | C | 2.34 g |
| Reductant | n-pentane | 2 mL | n-pentane | 2 mL | n-pentane | 1 mL | n-pentane | 1 mL |
| Light | UV | 1.8 h | UV | 2.5 h | UV | 18 h | UV | 18 h |
| Air | at end | | none | | at end | | none | |
| Hydrolysis | 4% $H_2O$/MeOH | 15 mL | 4% $H_2O$/MeOH | 15 mL | 4% $H_2O$/MeOH | 15 mL | 4% $H_2O$/MeOH | 15 mL |
| Acid or Base | none | | | | | | | |
| Redox Products/Cr | 0.656 | | 0 | | 0.706 | | 0 | |

TABLE I-continued

Summary of Examples 1-81 (products in mol %)

| Products | 2&3-pentanols | 68% | none | | 2&3-pentanols | 66% | none | |
| | 1-pentanol | 17% | | | 1-pentanol | 17% | | |
| | 3-pentanone | 6% | | | 3-pentanone | 7% | | |
| | 2-pentanone | 5% | | | 2-pentanone | 5% | | |
| | pentanal | 4% | | | pentanal | 5% | | |

| Examples 57-60 | 57 | Amount | 58 | Amount | 59 | Amount | 60 | Amount |
|---|---|---|---|---|---|---|---|---|
| Catalyst type | Cr(II) | | Cr(II) | | Cr(II) | | Cr(II) | |
| Catalyst/Amount | C | 1.61 g | C | 1.6 g | C | 2.19 g | C | 2.19 g |
| Reductant | n-pentane | 2 mL | n-pentane | 2 mL | n-hexane | | n-hexane | |
| Light | none | 3 min | none | 5 days | none | 2.5 h | none | 2.5 h |
| Air | at end | | at end | | at end | | none | |
| Hydrolysis | 7% H$_2$O/EtOH | 15 mL | 7% H$_2$O/EtOH | 15 mL | 7% H$_2$O/EtOH | 15 mL | 7% H$_2$O/EtOH | 15 mL |
| Acid or Base | 0.1% HCl | | 0.1% HCl | | 0.1% HCl | | 0.1% HCl | |
| Redox Products/Cr | 0.196 | | 0.668 | | 0.26 | | 0 | |
| Products | 2&3-pentanols | 71% | 2-pentanol | 87% | 2-hexanol | 40% | none | |
| | 1-pentanol | 13% | 3-pentanone | 7% | 3-hexanol | 34% | | |
| | 2-pentanone | 9% | 2-pentanone | | 1-hexanol | 11% | | |
| | 3-pentanone | 5% | pentanal | | 2-hexanone | 6% | | |
| | pentanal | 2% | | | 3-hexanone | 5% | | |
| | | | | | hexanal | 4% | | |

| Examples 61-64 | 61 | Amount | 62 | Amount | 63 | Amount | 64 | Amount |
|---|---|---|---|---|---|---|---|---|
| Catalyst type | Cr(II) | | Cr(II) | | Cr(II) | | Cr(II) | |
| Catalyst/Amount | C | 1.92 g | C | 1.92 g | C | 2.00 g | C | 2.06 g |
| Reductant | cyclopentane | 2 mL | cyclopentane | 2 mL | isopentane | 1 mL | isopentane | 2 mL |
| Light | none | 2.5 h | none | 2.5 h | none | 1.5 h | none | 2.6 h |
| Air | at end | | none | | at end | | none | |
| Hydrolysis | 7% H$_2$O/EtOH | 15 mL | 7% H$_2$O/EtOH | 15 mL | 7% H$_2$O/EtOH | 15 mL | 7% H$_2$O/EtOH | 15 mL |
| Acid or Base | 0.1% HCl | | 0.1% HCl | | 0.1% HCl | | 0.1% HCl | |
| Redox Products/Cr | 0.236 | | 0 | | 0.714 | | 0 | |
| Products | 2-cyclopenten-1-ol | 54% | none | | 2-Me-2-butanol | 40% | none | |
| | cyclopentanol | 38% | | | 3-Me-2-butanol | 41% | | |
| | cyclopentanone | 8% | | | 3-Me-1-butanol | 12% | | |
| | | | | | 2-Me-1-butanol | 4% | | |
| | | | | | 3-Me-2-butanone | 3% | | |

| Examples 65-68 | 65 | Amount | 66 | Amount | 67 | Amount | 68 | Amount |
|---|---|---|---|---|---|---|---|---|
| Catalyst type | Cr(II) | | Cr(II) | | Cr(II) | | Cr(II) | |
| Catalyst/Amount | C | 2.09 g | C | 2.04 g | C | 1.99 g | C | 1.92 g |
| Reductant | isopentane | 2 mL | benzene | 2 mL | benzene | 2 mL | toluene | 2 mL |
| Light | none | 2.6 h | none | 1.8 h | none | 1.8 h | none | 1.8 h |
| Air | at end | | at end | | none | | at end | |
| Hydrolysis | 7% H$_2$O/EtOH | 15 mL | 4% H$_2$O/MeOH | 15 mL | 4% H$_2$O/MeOH | 15 mL | 4% H$_2$O/MeOH | 15 mL |
| Acid or Base | 0.1% HCl | | none | | none | | none | |
| Redox Products/Cr | 0.142 | | 0.692 | | 0 | | 1.743 | |
| Products | 2-Me-2-butanol | 36% | phenol | 100% | none | | 2-Me-phenol | 35% |
| | 3-Me-2-butanol | 20% | | | | | | |
| | 2-Me-1-butanol | 18% | | | | | 4-Me-phenol | 34% |
| | 2-Me-pentanal | 11% | | | | | benzaldehyde | 12% |

TABLE I-continued

Summary of Examples 1-81 (products in mol %)

|  | 3-Me-1-butanol | 7% |  |  |  |  | benzyl alcohol | 10% |
|---|---|---|---|---|---|---|---|---|
|  | 3-Me-2-butanone | 5% |  |  |  |  | $C_{14}H_{14}$, 1-Me-2-(phenylmethyl)-benzene | 5% |
|  | 2-Me-butanal | 3% |  |  |  |  | $C_{14}H_{14}$, 2,2-diMe-1,1-biphenyl ? | 4% |

| Examples 69-72 | 69 | Amount | 70 | Amount | 71 | Amount | 72 | Amount |
|---|---|---|---|---|---|---|---|---|
| Catalyst type | Cr(II) |  | Cr(II) |  | Cr(II) |  | Cr(II) |  |
| Catalyst/Amount | C | 2.12 g | C | 2.03 g | C | 1.83 g | C | 1.79 g |
| Reductant | toluene | 2 mL | ethylbenzene | 2 mL | ethylbenzene | 2 mL | ethylene | 15 psi |
| Light | none | 1.8 h | none | 2.5 h | none | 2.5 h | none | 2 min |
| Air | none |  | at end |  | none |  | at end |  |
| Hydrolysis | 4% $H_2O$/MeOH | 15 mL | 7% $H_2O$/EtOH | 15 mL | 7% $H_2O$/EtOH | 15 mL | 5% $H_2O$/MeOH | 15 mL |
| Acid or Base | none |  | 0.1% HCl |  | 0.1% HCl |  | none |  |
| Redox Products/Cr | 0 |  | 0.318 |  | 0 |  | 1.0 |  |
| Products | none |  | 1-Ph-ethanol | 28% | none |  | acetaldehyde | 54% |
|  |  |  | 1-Ph-ethanone | 28% |  |  | formic acid | 46% |
|  |  |  | 2-et-phenol | 20% |  |  |  |  |
|  |  |  | 4-et-phenol | 13% |  |  |  |  |
|  |  |  | 3-et-phenol | 8% |  |  |  |  |
|  |  |  | $C_{16}H_{18}$ | 2% |  |  |  |  |
|  |  |  | benzaldehyde | 2% |  |  |  |  |

| Examples 73-76 | 73 | Amount | 74 | Amount | 75 | Amount | 76 | Amount |
|---|---|---|---|---|---|---|---|---|
| Catalyst type | Cr(II) |  | Cr(II) |  | Cr(II) |  | Cr(II) |  |
| Catalyst/Amount | C | 2.29 g | C | 2.36 g | C | 1.86 g | C | 2.16 g |
| Reductant | ethylene | 15 psi | ethylene | 15 psi | 1-pentene | 0.3 mL | 1-pentene | 2 mL |
| Light | none | 5 min | UV | 70 min | none | 1 h | none | 3.5 h |
| Air | at end |  | none |  | at end |  | none |  |
| Hydrolysis | 4% $H_2O$/MeOH | 15 mL | 5% $H_2O$/MeOH | 15 mL | 7% $H_2O$/EtOH | 15 mL | 7% $H_2O$/EtOH | 15 mL |
| Acid or Base | none |  | none |  | 0.1% HCl |  | 0.1% HCl |  |
| Redox Products/Cr | 0.999 |  | 0 |  | 0.180 |  | 0 |  |
| Products | acetaldehyde | 58% | none |  | pentanal | 21% | none |  |
|  | formic acid | 42% |  |  | C5 oxygenate | 15% |  |  |
|  |  |  |  |  | 3-pentanol | 14% |  |  |
|  |  |  |  |  | C5 oxygenate | 11% |  |  |
|  |  |  |  |  | $C_5H_{12}O$ | 10% |  |  |
|  |  |  |  |  | 1-penten-3-ol | 10% |  |  |
|  |  |  |  |  | C5 oxygenate | 6% |  |  |
|  |  |  |  |  | 4-penten-2-ol | 5% |  |  |
|  |  |  |  |  | $C_5H_{10}O$ | 4% |  |  |
|  |  |  |  |  | 2-pentenal | 2% |  |  |
|  |  |  |  |  | 3-pentanone | 2% |  |  |

| Examples 77-80 | 77 | Amount | 78 | Amount | 79 | Amount | 80 | Amount |
|---|---|---|---|---|---|---|---|---|
| Catalyst type | Cr(II) |  | Cr(II) |  | Cr(II) |  | Cr(II) |  |
| Catalyst/Amount | C | 1.77 g | C | 1.84 g | C | 2.06 g | C | 1.94 g |
| Reductant | 2-pentene | 0.5 mL | 1-hexene | 0.3 mL | 1-hexene | 2 mL | 1-hexene | 2 mL |
| Light | none | 1 h | none | 1 h | none | 1 h | UV | 2.5 h |
| Air | at end |  | at end |  | at end |  | none |  |
| Hydrolysis | 7% $H_2O$/EtOH | 15 mL | 7% $H_2O$/EtOH | 15 mL | 7% $H_2O$/EtOH | 15 mL | 7% $H_2O$/EtOH | 15 mL |
| Acid or Base | 0.1% HCl |  | 0.1% HCl |  | 0.1% HCl |  | 0.1% HCl |  |
| Redox Products/Cr | 2.322 |  | 0.498 |  | 0.339 |  | 0 |  |
| Products | pentanal | 18% | $C_6H_{12}O$ | 21% | C6 oxygenate | 53% | none |  |
|  | 3-pentanol | 13% | 1,2-hexanediol | 12% | $C_6H_{12}O$ | 15% |  |  |

TABLE I-continued

Summary of Examples 1-81 (products in mol %)

| | | | | | |
|---|---|---|---|---|---|
| 1-pentanol | 11% | C6 oxygenate | 12% | 3-hexen-1-ol | 6% |
| C5 oxygenate | 10% | C6 oxygenate | 9% | 1,2-hexanediol | 5% |
| 4-penten-2-ol | 9% | C6 oxygenate | 5% | C6 oxygenate | 5% |
| $C_5H_{10}O$ | 9% | $C_6H_{14}O_2$ | 5% | pentanal | 3% |
| C5 oxygenate | 7% | C6 oxygenate | 4% | $C_6H_{12}O$ | 2% |
| C5 oxygenate | 6% | $C_6H_{12}O$ | 4% | $C_6H_{12}O$ | 2% |
| 3 or 4-penten-2-ol | 5% | C6 oxygenate | 3% | C6 oxygenate | 2% |
| 3-penten-2-one | 2% | $C_6H_{12}O$ | 3% | 2-hexanone | 2% |
| 3-pentanone | 2% | C6 oxygenate | 3% | 1-hexen-3-ol | 1% |
| 2-Me-2-butenal | 2% | 1-hexen-3-ol | 3% | $C_6H_{13}ClO$ | 1% |
| 2-pentenal | 2% | butanal | 3% | $C_6H_{13}ClO$ | 1% |
| pentenal | 1% | 2-hexenal | 2% | $C_8H_{18}O_2$ or $C_6H_{14}O_2$ | 1% |
| 1-penten-3-ol | 1% | $C_6H_{14}O_2$ | 2% | | |

| Example 81 | 81 | Amount |
|---|---|---|
| Catalyst type | Cr(II) | |
| Catalyst/Amount | C | 1.67 g |
| Reductant | cyclohexene | 0.5 mL |
| Light | none | 1 h |
| Air | at end | |
| Hydrolysis | 7% $H_2O$/EtOH | 15 mL |
| Acid or Base | 0.1% HCl | |
| Redox Products/Cr | 0.598 | |
| Products | $C_{12}H_{20}O_2$ | 32% |
| | 2-cyclohexen-1-ol | 25% |
| | 2-cyclohexyl-cyclohexanone | 20% |
| | 2-cyclohexen-1-one | 12% |
| | 1,2-cyclohexanediol | 4% |
| | $C_{12}H_{20}O$ | 2% |
| | C12 oxygenate | 2% |
| | $C_{12}H_{18}O$ | 1% |
| | $C_{12}H_{20}O$ | 1% |
| | C12 oxygenate | 1% |
| | C12 oxygenate | 1% |

TABLE II

Oxygenated Oligomers (products in moles per mole of chromium)

| Example | Reductant | Catalyst Type | Dimers | Trimers | Tetramers | Comment |
|---|---|---|---|---|---|---|
| 24 | 1-pentene | Cr(VI) | 2.026 | 0.572 | 0.713 | air |
| 25 | 1-pentene | Cr(VI) | 1.196 | 0.284 | 0.635 | no air |
| A | 1-pentene | Cr(VI) | 0.048 | 0 | 0.048 | no air |
| B | 1-pentene | Cr(VI) | 0.063 | 0.013 | 0.920 | air |
| 27 | 1-pentene | Cr(VI) | 0.128 | 0.037 | 0.248 | no air |
| 26 | 1-pentene | Cr(VI) | 0.631 | 0.161 | 0.175 | air |
| 28 | 1-pentene | Cr(VI) | 0.109 | 0.054 | 0.005 | air |
| 29 | 1-pentene | Cr(VI) | 0.322 | 0.088 | 0.127 | no air |
| C | 1-pentene | Cr(VI) | 0.698 | 0 | 0 | no air |
| D | 1-pentene | Cr(VI) | 0.014 | 0.008 | 0 | no air |
| E | 1-pentene | Cr(VI) | 0.024 | 0.001 | 0 | no air |
| F | 1-pentene | Cr(VI) | 0.124 | 0 | 0 | no air |
| 31 | 2-pentene | Cr(VI) | 0.156 | 0 | 0 | no air |
| 30 | 2-pentene | Cr(VI) | 0.213 | 0 | 0 | air |
| G | cyclopentene | Cr(VI) | 0.233 | 0 | 0 | no air |
| 35 | cyclopentene | Cr(VI) | 0.049 | 0.002 | 0 | no air |
| 34 | cyclopentene | Cr(VI) | 0.047 | 0.002 | 0 | air |
| 37 | 1-hexene | Cr(VI) | 6.55 | 1.416 | 0 | air |
| H | 1-hexene | Cr(VI) | 0.98 | 0.654 | 0.032 | no air |
| I | 1-hexene | Cr(VI) | 1.89 | 0.599 | 0 | no air |
| J | 1-hexene | Cr(VI) | 1.46 | 0.474 | 0 | no air |
| 40 | 1-hexene | Cr(VI) | 0.00 | 0.211 | 0 | no air |
| 39 | 1-hexene | Cr(VI) | 0.50 | 0.124 | 0.024 | air |
| 42 | 1-hexene | Cr(VI) | 0.69 | 0.837 | 0.246 | no air |
| 41 | 1-hexene | Cr(VI) | 5.01 | 1.012 | 0.070 | air |
| 36 | 1-hexene | Cr(VI) | 1.13 | 0 | 0 | air |
| 38 | 1-hexene | Cr(VI) | 0.85 | 0.247 | 0 | no air |
| K | 1-hexene | Cr(VI) | 0.05 | 0 | 0 | no air |
| L | 1-hexene | Cr(VI) | 0.16 | 0 | 0 | no air |
| M | 1-hexene | Cr(VI) | 0.24 | 0 | 0 | no air |
| N | 1-hexene | Cr(VI) | 0.01 | 0 | 0 | no air |
| O | 1-hexene | Cr(VI) | 0.01 | 0 | 0 | no air |
| P | 1-hexene | Cr(VI) | 0.00 | 0.002 | 0 | no air |
| Q | 1-hexene | Cr(VI) | 0.00 | 0.001 | 0 | no air |
| R | 1-hexene | Cr(VI) | 0.084 | 1.011 | 0 | no air |
| S | 1-hexene | Cr(VI) | 0.102 | 1.083 | 0 | air |
| 44 | cyclohexene | Cr(VI) | 0.223 | 0 | 0 | air |
| 43 | cyclohexene | Cr(VI) | 0.258 | 0 | 0 | air |
| 45 | cyclohexene | Cr(VI) | 0.119 | 0 | 0 | no air |
| 46 | cyclohexene | Cr(VI) | 0.164 | 0 | 0 | air |
| 48 | cyclohexene | Cr(VI) | 0.036 | 0 | 0 | no air |
| 47 | cyclohexene | Cr(VI) | 0.044 | 0 | 0 | air |
| 78 | 1-hexene | Cr(II) | 0.039 | 0.006 | 0 | air |
| 80 | 1-hexene | Cr(II) | 0.00 | 0 | 0 | no air |
| 81 | cyclohexene | Cr(II) | 0.460 | 0.009 | 0 | air |

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process for converting a hydrocarbon reactant into an alcohol compound and/or a carbonyl compound, the process comprising:

(i) irradiating, in an oxidizing atmosphere, the hydrocarbon reactant and a supported chromium catalyst comprising chromium in a hexavalent oxidation state with a light beam at a wavelength in the UV-visible spectrum to reduce at least a portion of the supported chromium catalyst to form a reduced chromium catalyst (e.g., with at least a portion of the chromium on the reduced chromium catalyst having at least one bonding site with a hydrocarboxy group (—O-hydrocarbon group)); and (ii) hydrolyzing the reduced chromium catalyst to form a reaction product comprising the alcohol compound and/or the carbonyl compound; or (i) contacting, in an oxidizing atmosphere, the hydrocarbon reactant comprising an olefin and a supported chromium catalyst comprising chromium in a hexavalent oxidation state to reduce at least a portion of the supported chromium catalyst to form a reduced chromium catalyst (e.g., with at least a portion of the chromium on the reduced chromium catalyst having at least one bonding site with a hydrocarboxy group (a —O-hydrocarbon group)); and (ii) hydrolyzing the reduced chromium catalyst to form a reaction product comprising the alcohol compound and/or the carbonyl compound (e.g., an allylic alcohol).

Aspect 2. A process for converting a hydrocarbon reactant into an alcohol compound and/or a carbonyl compound, the process comprising:

(I) irradiating the hydrocarbon reactant and a supported chromium catalyst comprising chromium in a hexavalent oxidation state with a light beam at a wavelength in the UV-visible spectrum to reduce at least a portion of the supported chromium catalyst to form a reduced chromium catalyst (e.g., with at least a portion of the chromium on the reduced chromium catalyst having at least one bonding site with a hydrocarboxy group (—O-hydrocarbon group));

(II) subjecting the reduced chromium catalyst to an oxidizing atmosphere; and (III) hydrolyzing the reduced chromium catalyst to form a reaction product comprising the alcohol compound and/or the carbonyl compound; or (I) contacting the hydrocarbon reactant comprising an olefin and a supported chromium catalyst comprising chromium in a hexavalent oxidation state to reduce at least a portion of the supported chromium catalyst to form a reduced chromium catalyst (e.g., with at least a portion of the chromium on the reduced chromium catalyst having at least one bonding site with a hydrocarboxy group (—O-hydrocarbon group));

(II) subjecting the reduced chromium catalyst to an oxidizing atmosphere; and (III) hydrolyzing the reduced chromium catalyst to form a reaction product comprising the alcohol compound and/or the carbonyl compound (e.g., an allylic alcohol).

Aspect 3. The process defined in aspect 1 or 2, wherein the reduced chromium catalyst in step (i) or step (I) comprises any suitable amount of chromium in an average oxidation state of +5 or less, or an amount in any range disclosed herein, e.g., from 0.01 to 50 wt. %, from 0.01 to 10 wt. %, from 0.05 to 15 wt. %, from 0.1 to 15 wt. %, from 0.2 to 10 wt. %, from 0.1 to 5 wt. %, from 0.5 to 30 wt. %, or from 0.5 to 2.5 wt. % of chromium in an average oxidation state of +5 or less, based on the weight of the reduced chromium catalyst.

Aspect 4. The process defined in any one of the preceding aspects, wherein the amount of the chromium of the supported chromium catalyst in a hexavalent oxidation state in step (i) or step (I) is at least 10 wt. %, at least 20 wt. %, at least 40 wt. %, at least 60 wt. %, at least 80 wt. %, or at least 90 wt. %, based on the total amount of chromium on the supported chromium catalyst, and/or the amount of chromium of the reduced chromium catalyst in a hexavalent oxidation state in step (i) or step (I) is (from 0 wt. %, from 0.5 wt. %, from 1 wt. %, or from 2 wt. % to) less than or equal to 50 wt. %, less than or equal to 40 wt. %, less than or equal to 30 wt. %, or less than or equal to 15 wt. %, based on the total amount of chromium on the reduced chromium catalyst.

Aspect 5. The process defined in any one of the preceding aspects, wherein at least 10 wt. %, at least 20 wt. %, at least 40 wt. %, at least 60 wt. %, at least 80 wt. %, or at least 90 wt. %, of the supported chromium catalyst is reduced to form the reduced chromium catalyst in step (i) or step (I), based on the total amount of the supported chromium catalyst.

Aspect 6. The process defined in any one of the preceding aspects, wherein the chromium in the reduced chromium catalyst in step (i) or step (I) has an average valence of less than or equal to 5.5, less than or equal to 5.25, less than or equal to 5, less than or equal to 4.5, less than or equal to 4.25, or less than or equal to 4.

Aspect 7. The process defined in any one of aspects 1-6, wherein the wavelength comprises a single wavelength or a range of wavelengths in the visible spectrum (from 380 nm to 780 nm).

Aspect 8. The process defined in any one of aspects 1-6, wherein the wavelength comprises a single wavelength or a range of wavelengths in the 200 nm to 750 nm range.

Aspect 9. The process defined in any one of aspects 1-6, wherein the wavelength comprises a single wavelength or a range of wavelengths in the 300 to 750 nm range, the 350 nm to 650 nm range, the 300 nm to 500 nm range, or the 300 nm to 400 nm range.

Aspect 10. The process defined in any one of aspects 1-6, wherein the wavelength comprises a single wavelength or a range of wavelengths below 600 nm, below 500 nm, below 475 nm, below 450 nm, below 430 nm, or below 420 nm.

Aspect 11. The process defined in any one of aspects 1-10, wherein the wavelength is a single wavelength.

Aspect 12. The process defined in any one of aspects 1-10, wherein the wavelength is a range of wavelengths spanning at least 25 nm, at least 50 nm, at least 100 nm, or at least 200 nm.

Aspect 13. The process defined in any one of the preceding aspects, wherein the light beam has any suitable intensity or an intensity in any range disclosed herein, e.g., at least 500 lumens, at least 1000 lumens, at least 2000 lumens, at least 5000 lumens, at least 10,000 lumens, or at least 20,000 lumens.

Aspect 14. The process defined in any one of the preceding aspects, wherein the light beam is from a light source having any suitable power or any power disclosed herein, e.g., at least 50 watts, at least 100 watts, at least 200 watts, at least 500 watts, at least 1,000 watts, or at least 2,000 watts.

Aspect 15. The process defined in any one of the preceding aspects, wherein the supported chromium catalyst is irradiated with any suitable illuminance or any illuminance disclosed herein, e.g., at least 100 lux, at least 500 lux, at least 1000 lux, at least 2000 lux, at least 5000 lux, at least 10,000 lux, at least 20,000 lux, at least 50,000 lux, or at least 100,000 lux.

Aspect 16. The process defined in any one of the preceding aspects, wherein the irradiating step (or contacting step) is conducted at any suitable temperature or any temperature disclosed herein, e.g., less than 200° C., less than 100° C., less than 40° C., from −100° C. to 100° C., from 0° C. to 100° C., or from 10° C. to 40° C.

Aspect 17. The process defined in any one of the preceding aspects, wherein the irradiating step (or contacting step) is conducted for any suitable exposure time or for any exposure time disclosed herein, e.g., from 15 sec to 48 hr, from 1 min to 6 hr, from 1 min to 15 min, or from 1 hr to 8 hr.

Aspect 18. The process defined in any one of the preceding aspects, wherein the molar ratio of the hydrocarbon reactant (or the molar ratio of elemental oxygen or other oxidizing agent) to chromium (of the supported chromium catalyst or the reduced chromium catalyst) is in any suitable range or any range disclosed herein, e.g., at least 0.25:1, at least 0.5:1, at least 1:1, at least 10:1, at least 100:1, at least 1000:1, or at least 10,000:1.

Aspect 19. The process defined in any one of aspects 1-18, wherein the process comprises irradiating (or contacting) a slurry of the supported chromium catalyst in the hydrocarbon reactant.

Aspect 20. The process defined in any one of aspects 1-18, wherein the process comprises contacting the hydrocarbon reactant with a fluidized bed of the supported chromium catalyst, and irradiating while contacting (fluidizing).

Aspect 21. The process defined in any one of aspects 1-18, wherein the process comprises contacting the hydrocarbon reactant (e.g., in a gas phase or in a liquid phase) with a fixed bed of the supported chromium catalyst, and irradiating while contacting.

Aspect 22. The process defined in any one of the preceding aspects, wherein the step of irradiating (or contacting) the hydrocarbon reactant with the supported chromium catalyst is conducted at any suitable WHSV or a WHSV in any range disclosed herein, e.g., from 0.01 hr$^{-1}$ to 500 hr$^{-1}$, or from 0.1 hr$^{-1}$ to 10 hr$^{-1}$.

Aspect 23. The process defined in any one of the preceding aspects, wherein the yield to the alcohol compound (or the carbonyl compound) per mole of chromium (VI) in the supported chromium catalyst is any molar ratio based on moles of chromium (VI) disclosed herein, e.g., at least 0.01, at least 0.025, at least 0.05, at least 0.1, or at least 0.25 moles (and up to 10, up to 8, up to 5, up to 3, up to 2, up to 1.5, or up to 1 mole) of the alcohol compound (or the carbonyl compound).

Aspect 24. A process for converting a hydrocarbon reactant (e.g., an olefin) into an alcohol compound and/or a carbonyl compound, the process comprising:
(a) contacting the hydrocarbon reactant (e.g., the olefin) and a supported chromium (II) catalyst (with or without irradiation) to form a treated chromium catalyst;
(b) subjecting the treated chromium catalyst to an oxidizing atmosphere; and
(c) hydrolyzing the treated chromium catalyst to form a reaction product comprising the alcohol compound and/or the carbonyl compound (e.g., an allylic alcohol).

Aspect 25. The process defined in aspect 24, wherein the supported chromium (II) catalyst in step (a) comprises any suitable amount of chromium (II) or an amount in any range disclosed herein, e.g., from 0.01 to 50 wt. %, from 0.01 to 10 wt. %, from 0.05 to 15 wt. %, from 0.1 to 15 wt. %, from 0.2 to 10 wt. %, from 0.1 to 5 wt. %, from 0.5 to 30 wt. %, or from 0.5 to 2.5 wt. % of chromium (II), based on the weight of the supported chromium (II) catalyst.

Aspect 26. The process defined in aspect 24 or 25, wherein the supported chromium (II) catalyst in step (a) comprises at least 20 wt. %, at least 50 wt. %, at least 75 wt. %, at least 85 wt. %, at least 90 wt. %, or at least 95 wt. % of chromium (II), based on the total amount of chromium, and/or the supported chromium (II) catalyst in step (a) comprises (from 0 wt. %, from 0.5 wt. %, from 1 wt. %, or from 2 wt. %) to less than or equal to 50 wt. %, less than or equal to 35 wt. %, less than or equal to 20 wt. %, or less than or equal to 10 wt. % of chromium (VI), based on the total amount of chromium.

Aspect 27. The process defined in any one of aspects 24-26, wherein the chromium in the supported chromium (II) catalyst in step (a) has an average valence of less than or equal to 3.5, less than or equal to 3.25, or less than or equal to 3, less than or equal to 2.5.

Aspect 28. The process defined in any one aspects 24-27, wherein the contacting step is conducted at any suitable temperature or any temperature disclosed herein, e.g., less than 200° C., less than 100° C., less than 40° C., from −100° C. to 100° C., from 0° C. to 100° C., or from 10° C. to 40° C.

Aspect 29. The process defined in any one of aspects 24-28, wherein the contacting step is conducted for any suitable contact time or for any contact time disclosed herein, e.g., from 15 sec to 48 hr, from 1 min to 6 hr, from 1 min to 15 min, or from 1 hr to 8 hr.

Aspect 30. The process defined in any one of aspects 24-29, wherein the molar ratio of the hydrocarbon reactant (or the molar ratio of elemental oxygen or other oxidizing agent) to chromium (of the supported chromium (II) catalyst or the treated chromium catalyst) is in any suitable range or any range disclosed herein, e.g., at least 0.25:1, at least 0.5:1, at least 1:1, at least 10:1, at least 100:1, at least 1000:1, or at least 10,000:1.

Aspect 31. The process defined in any one of aspects 24-30, wherein the process comprises slurrying the supported chromium (II) catalyst in the hydrocarbon reactant.

Aspect 32. The process defined in any one of aspects 24-30, wherein the process comprises contacting the hydrocarbon reactant with a fluidized bed of the supported chromium (II) catalyst.

Aspect 33. The process defined in any one of aspects 24-30, wherein the process comprises contacting the hydrocarbon reactant (e.g., in a gas phase or in a liquid phase) with a fixed bed of the supported chromium (II) catalyst.

Aspect 34. The process defined in any one of aspects 24-33, wherein the step of contacting the hydrocarbon reactant and the supported chromium (II) catalyst is conducted at any suitable WHSV or a WHSV in any range disclosed herein, e.g., from 0.01 hr$^{-1}$ to 500 hr$^{-1}$, or from 0.1 hr$^{-1}$ to 10 hr$^{-1}$.

Aspect 35. The process defined in any one of aspects 24-34, wherein the yield to the alcohol compound (or the carbonyl compound) per mole of chromium (II) in the supported chromium (II) catalyst is any molar ratio based on moles of chromium (II) disclosed herein, e.g., at least 0.01, at least 0.025, at least 0.05, at least 0.1, or at least 0.25 moles (and up to 10, up to 8, up to 5, up to 3, up to 2, up to 1.5, or up to 1 mole) of the alcohol compound (or the carbonyl compound).

Aspect 36. The process defined in any one of aspects 1-35, wherein the hydrocarbon reactant comprises a saturated or an unsaturated, linear or branched or cyclic, aliphatic hydrocarbon, and including combinations thereof.

Aspect 37. The process defined in any one of aspects 1-35, wherein the hydrocarbon reactant comprises an aromatic compound (e.g., benzene, toluene, xylene, styrene, and substituted versions thereof, and including combinations thereof).

Aspect 38. The process defined in any one of aspects 1-35, wherein the hydrocarbon reactant comprises a linear alkane compound, a branched alkane compound, a cyclic alkane compound, or a combination thereof.

Aspect 39. The process defined in any one of aspects 1-35, wherein the hydrocarbon reactant comprises a linear olefin compound (e.g., an α-olefin), a branched olefin compound, a cyclic olefin compound, or a combination thereof.

Aspect 40. The process defined in any one of aspects 1-35, wherein the hydrocarbon reactant comprises any suitable carbon number alkane compound or any carbon number alkane compound disclosed herein, e.g., a $C_1$ to $C_{36}$ alkane compound, a $C_1$ to $C_{18}$ alkane compound, a $C_1$ to $C_{12}$ alkane compound, or a $C_1$ to $C_8$ alkane compound; and/or the hydrocarbon reactant comprises any suitable carbon number olefin compound or any carbon number olefin compound disclosed herein, e.g., a $C_2$ to $C_{36}$ olefin compound, a $C_2$ to $C_{18}$ olefin compound, a $C_2$ to $C_{12}$ olefin compound, or a $C_2$ to $C_8$ olefin compound; and/or the hydrocarbon reactant comprises any suitable carbon number aromatic compound or any carbon number aromatic compound disclosed herein, e.g., a $C_6$ to $C_{36}$ aromatic compound, a $C_6$ to $C_{18}$ aromatic compound, a $C_6$ to $C_{12}$ aromatic compound, or a $C_6$ to $C_8$ aromatic compound.

Aspect 41. The process defined in any one of aspects 1-35, wherein the hydrocarbon reactant comprises methane, ethane, propane, butane (e.g., n-butane or isobutane), pentane (e.g., n-pentane, neopentane, cyclopentane, or isopentane), hexane, heptane, octane, nonane, decane, undecane, dodecane, tridecane, tetradecane, pentadecane, hexadecane, heptadecane, octadecane, or any combination thereof or the hydrocarbon reactant comprises methane, ethane, propane, n-butane, isobutane, n-pentane, neopentane, isopentane, n-hexane, n-heptane, n-octane, n-decane, n-dodecane, or any combination thereof; or the hydrocarbon reactant comprises methane, ethane, propane, butane, pentane, hexane, or any combination thereof.

Aspect 42. The process defined in any one of aspects 1-35, wherein the hydrocarbon reactant comprises ethylene, propylene, 1-butene, 1-pentene, 2-pentene, 1-hexene, 1-heptene, 1-octene, 1-decene, 1-dodecene, 1-tetradecene, 1-hexadecene, 1-octadecene, cyclopentene, cyclohexene, or any combination thereof.

Aspect 43. The process defined in any one of aspects 1-35, wherein the hydrocarbon reactant comprises benzene, toluene, ethylbenzene, xylene, styrene, mesitylene, or any combination thereof.

Aspect 44. The process defined in any one of aspects 1-35, wherein the hydrocarbon reactant comprises a $C_n$ hydrocarbon compound, the alcohol compound comprises a $C_n$ alcohol compound, and the carbonyl compound comprises a $C_n$ carbonyl compound.

Aspect 45. The process defined in aspect 44, wherein n is any suitable integer or an integer in any range disclosed herein, e.g., from 1 to 36, from 1 to 18, from 1 to 12, or from 1 to 8.

Aspect 46. The process defined in any one of aspects 1-35, wherein the hydrocarbon reactant comprises methane (or ethane), and the alcohol compound comprises methanol (or ethanol).

Aspect 47. The process defined in any one of the preceding aspects, wherein the supported chromium catalyst (or the reduced chromium catalyst, or the supported chromium (II) catalyst, or the treated chromium catalyst) comprises any suitable amount of chromium or an amount in any range disclosed herein, e.g., from 0.01 to 50 wt. %, from 0.01 to 10 wt. %, from 0.05 to 15 wt. %, from 0.1 to 15 wt. %, from 0.2 to 10 wt. %, from 0.1 to 5 wt. %, from 0.5 to 30 wt. %, or from 0.5 to 2.5 wt. % of chromium, based on the weight of the respective catalyst.

Aspect 48. The process defined in any one of aspects 1-47, wherein the supported chromium catalyst (or the reduced chromium catalyst, or the supported chromium (II) catalyst, or the treated chromium catalyst) comprises any suitable solid oxide or any solid oxide disclosed herein, e.g., silica, alumina, silica-alumina, silica-coated alumina, aluminum phosphate, aluminophosphate, heteropolytungstate, titania, zirconia, magnesia, boria, zinc oxide, silica-titania, silica-zirconia, alumina-titania, alumina-zirconia, zinc-aluminate, alumina-boria, alumina borate, silica-boria, aluminophosphate-silica, titania-zirconia, or any combination thereof.

Aspect 49. The process defined in any one of aspects 1-47, wherein the supported chromium catalyst (or the reduced chromium catalyst, or the supported chromium (II) catalyst, or the treated chromium catalyst) comprises silica, silica-alumina, silica-coated alumina, silica-titania, silica-titania-magnesia, silica-zirconia, silica-magnesia, silica-boria, aluminophosphate-silica, alumina, alumina borate, or any combination thereof.

Aspect 50. The process defined in any one of aspects 1-47, wherein the supported chromium catalyst (or the reduced chromium catalyst, or the supported chromium (II) catalyst, or the treated chromium catalyst) comprises a chemically-treated solid oxide comprising a solid oxide (e.g., as in aspect 48 or 49, such as silica, alumina, silica-alumina, silica-titania, silica-zirconia, silica-yttria, aluminophosphate, zirconia, titania, thoria, or stania) treated with an electron-withdrawing anion.

Aspect 51. The process defined in aspect 50, wherein the electron-withdrawing anion comprises sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, tungstate, molybdate, or any combination thereof.

Aspect 52. The process defined in aspect 50 or 51, wherein the chemically-treated solid oxide contains from 1 to 30 wt. %, from 2 to 20 wt. %, from 2 to 15 wt. %, from 2 to 10 wt. %, or from 3 to 10 wt. %, of the electron-withdrawing anion, based on the total weight of the chemically-treated solid oxide.

Aspect 53. The process defined in any one of aspects 1-47, wherein the supported chromium catalyst (or the reduced chromium catalyst, or the supported chromium (II) catalyst, or the treated chromium catalyst) comprises a chemically-treated solid oxide comprising fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, or any combination thereof.

Aspect 54. The process defined in any one of aspects 1-47, wherein the supported chromium catalyst (or the reduced chromium catalyst, or the supported chromium (II) catalyst, or the treated chromium catalyst) comprises chromium/silica, chromium/silica-titania, chromium/silica-titania-magnesia, chromium/silica-alumina, chromium/silica-coated alumina, chromium/aluminophosphate, chromium/alumina, chromium/alumina borate, or any combination thereof.

Aspect 55. The process defined in any one of aspects 1-47, wherein the supported chromium catalyst (or the reduced chromium catalyst, or the supported chromium (II) catalyst, or the treated chromium catalyst) comprises chromium/silica-titania, and the respective catalyst comprises any suitable amount of titanium or an amount in any range disclosed herein, e.g., from 0.1 to 20 wt. %, from 0.5 to 15 wt. %, from 1 to 10 wt. %, or from 1 to 6 wt. %, based on the weight of the respective catalyst.

Aspect 56. The process defined in any one of aspects 1-47, wherein the supported chromium catalyst (or the reduced chromium catalyst, or the supported chromium (II) catalyst, or the treated chromium catalyst) comprises chromium/sulfated alumina, chromium/fluorided alumina, chromium/fluorided silica-alumina, chromium/fluorided silica-coated alumina, or any combination thereof.

Aspect 57. The process defined in any one of aspects 1-47, wherein the supported chromium catalyst (or the reduced chromium catalyst, or the supported chromium (II) catalyst, or the treated chromium catalyst) comprises a zeolite.

Aspect 58. The process defined in aspect 57, wherein the supported chromium catalyst (or the reduced chromium catalyst, or the supported chromium (II) catalyst, or the treated chromium catalyst) comprises a medium pore zeolite, a large pore zeolite, or a combination thereof.

Aspect 59. The process defined in aspect 57, wherein the zeolite comprises a ZSM-5 zeolite, a ZSM-11 zeolite, an EU-1 zeolite, a ZSM-23 zeolite, a ZSM-57 zeolite, an ALPO4-11 zeolite, an ALPO4-41 zeolite, a Ferrierite framework type zeolite, or a combination thereof.

Aspect 60. The process defined in aspect 57, wherein the supported chromium catalyst (or the reduced chromium catalyst, or the supported chromium (II) catalyst, or the treated chromium catalyst) comprises an L-zeolite, a Y-zeolite, a mordenite, an omega zeolite, and/or a beta zeolite.

Aspect 61. The process defined in any one of aspects 57-60, wherein the supported chromium catalyst (or the reduced chromium catalyst, or the supported chromium (II) catalyst, or the treated chromium catalyst) comprises the zeolite and any suitable amount of binder or an amount in any range disclosed herein, e.g., from 3 wt. % to 35 wt. %, or from 5 wt. % to 30 wt. % binder, based on the weight of the respective catalyst.

Aspect 62. The process defined in any one of the preceding aspects, wherein the supported chromium catalyst (or the reduced chromium catalyst, or the supported chromium (II) catalyst, or the treated chromium catalyst) has any suitable pore volume (total) or a pore volume (total) in any range disclosed herein, e.g., from 0.1 to 5 mL/g, from 0.15 to 5 mL/g, from 0.1 to 3 mL/g, from 0.15 to 2 mL/g, from 0.3 to 1.5 mL/g, or from 0.5 to 1.0 mL/g.

Aspect 63. The process defined in any one of the preceding aspects, the supported chromium catalyst (or the reduced chromium catalyst, or the supported chromium (II) catalyst, or the treated chromium catalyst) has any suitable BET surface area or a BET surface area in any range disclosed herein, e.g., from 50 to 2000 m$^2$/g, from 50 to 700 m$^2$/g, from 50 to 400 m$^2$/g, from 100 to 1200 m$^2$/g, or from 150 to 525 m$^2$/g.

Aspect 64. The process defined in any one of the preceding aspects, wherein the supported chromium catalyst (or the reduced chromium catalyst, or the supported chromium (II) catalyst, or the treated chromium catalyst) is in any suitable shape or form or any shape or form disclosed herein, e.g., powder, round or spherical (e.g., spheres), ellipsoidal, pellet, bead, cylinder, granule (e.g., regular and/or irregular), trilobe, quadralobe, ring, wagonwheel, monolith, or any combination thereof.

Aspect 65. The process defined in any one aspects 1-64, wherein the supported chromium catalyst (or the reduced chromium catalyst, or the supported chromium (II) catalyst, or the treated chromium catalyst) has any suitable average (d50) particle size or an average (d50) particle size in any range disclosed herein, e.g., from 10 to 500 microns, from 25 to 250 microns, or from 20 to 100 microns.

Aspect 66. The process defined in any one aspects 1-64, wherein the supported chromium catalyst (or the reduced chromium catalyst, or the supported chromium (II) catalyst, or the treated chromium catalyst) comprises pellets or beads having any suitable average size or an average size in any range disclosed herein, e.g., from 1/16 inch to 1/2 inch, or from 1/8 inch to 1/4 inch.

Aspect 67. The process defined in any one of aspects 1-66, wherein the hydrocarbon reactant is in a gas phase during the irradiating (or contacting) step.

Aspect 68. The process defined in any one of aspects 1-66, wherein the hydrocarbon reactant is in a liquid phase during the irradiating (or contacting) step.

Aspect 69. The process defined in any one of the preceding aspects, wherein the hydrolyzing step is conducted at any suitable temperature or any temperature disclosed herein, e.g., less than 200° C., less than 100° C., less than 40° C., from 0° C. to 100° C., or from 10° C. to 40° C.

Aspect 70. The process defined in any one of the preceding aspects, wherein the hydrolyzing step comprises contacting the reduced chromium catalyst (or the treated chromium catalyst) with a hydrolysis agent.

Aspect 71. The process defined in aspect 70, wherein the hydrolysis agent comprises any suitable hydrolysis agent or any hydrolysis agent disclosed herein, e.g., water, steam, an alcohol agent, an acid agent, an alkaline agent, or any combination thereof.

Aspect 72. The process defined in aspect 70, wherein the hydrolysis agent further comprises any suitable reducing agent or any reducing agent disclosed herein, e.g., ascorbic acid, an iron (II) reducing agent, ferrous (II) ions, a zinc reducing agent, sodium bisulfite, sodium thiosulfate, sodium sulfide, or any combination thereof.

Aspect 73. The process defined in any one of the preceding aspects, wherein the carbonyl compound comprises an aldehyde compound, a ketone compound, an organic acid compound, or any combination thereof; additionally or alternatively, the alcohol compound comprises a diol, an allylic alcohol, a phenol, or any combination thereof.

Aspect 74. The process defined in any one of the preceding aspects, wherein a conversion of the hydrocarbon reactant (or a yield to the alcohol compound, or a yield to the carbonyl compound) is any percent conversion (or yield) disclosed herein, e.g., at least 2 wt. %, at least 5 wt. %, at least 10 wt. %, or at least 15 wt. % (and up to 99 wt. %, 95 wt. %, 90 wt. %, 80 wt. %, 70 wt. %, or 50 wt. %).

Aspect 75. The process defined in any one of the preceding aspects, wherein a single pass conversion of the hydrocarbon reactant (or a single pass yield to the alcohol compound, or a single pass yield to the carbonyl compound) is any single pass percent conversion (or single pass yield) disclosed herein, e.g., at least 2 wt. %, at least 5 wt. %, at least 10 wt. %, or at least 15 wt. % (and up to 99 wt. %, 95 wt. %, 90 wt. %, 80 wt. %, 70 wt. %, or 50 wt. %).

Aspect 76. The process defined in any one of the preceding aspects, further comprising a step of separating at least a portion (and in some cases, all) of the hydrocarbon reactant from the reaction product after the hydrolyzing step to produce a separated hydrocarbon portion using any suitable technique or any technique disclosed herein, e.g., extraction, filtration, evaporation, distillation, or any combination thereof.

Aspect 77. The process defined in aspect 76, wherein the separated hydrocarbon portion is recycled and irradiated (or contacted) with the supported chromium catalyst (or the supported chromium (II) catalyst) again.

Aspect 78. The process defined in any one of the preceding aspects, further comprising a step of separating at least a portion (and in some cases, all) of the alcohol compound and/or the carbonyl compound from the reaction product using any suitable technique or any technique disclosed herein, e.g., extraction, filtration, evaporation, distillation, or any combination thereof.

Aspect 79. The process defined in any one of the preceding aspects, further comprising a step of separating at least a portion (and in some cases, all) of the reduced chromium catalyst (or the treated chromium catalyst) from the reaction product after the hydrolyzing step to produce a separated reduced chromium catalyst (or a separated treated chromium catalyst) using any suitable technique or any technique disclosed herein, e.g., extraction, filtration, evaporation, distillation, or any combination thereof.

Aspect 80. The process defined in any one of aspects 1-23 or 36-79, further comprising a step of calcining the reduced chromium catalyst or the separated reduced chromium catalyst to regenerate the supported chromium catalyst.

Aspect 81. The process defined in aspect 80, wherein calcining comprises subjecting the reduced chromium catalyst or the separated reduced chromium catalyst to an oxidizing atmosphere at any suitable peak temperature and time conditions or any peak temperature and time conditions disclosed herein, e.g., a peak temperature from 300° C. to 1000° C., from 500° C. to 900° C., or from 550° C. to 870° C., for a time period of from 1 min to 24 hr, from 1 hr to 12 hr, or from 30 min to 8 hr.

Aspect 82. The process defined in any one of aspects 24-79, further comprising a step of reducing the treated chromium catalyst or the separated treated chromium catalyst to regenerate the supported chromium (II) catalyst.

Aspect 83. The process defined in aspect 82, wherein reducing comprises subjecting the treated chromium catalyst or the separated treated chromium catalyst to a reducing atmosphere, e.g., CO reduction, UV light reduction, elevated temperature reduction, or any combination thereof.

Aspect 84. The process defined in any one of the preceding aspects, wherein the oxidizing atmosphere comprises any suitable oxidizing atmosphere or any oxidizing atmosphere disclosed herein, e.g., oxygen, air, a mixture of air and an inert gas (such as nitrogen), a mixture of oxygen and an inert gas, NO, $NO_2$, $N_2O$, ozone, a halide oxide, $H_2O_2$, an organic peroxide, as well as combinations thereof.

Aspect 85. The process defined in any one of aspects 2-84, wherein the subjecting step is conducted at any suitable temperature or any temperature disclosed herein, e.g., less than 200° C., less than 100° C., less than 40° C., from −100° C. to 100° C., from 0° C. to 100° C., or from 10° C. to 40° C.

Aspect 86. The process defined in any one of aspects 2-85, wherein the subjecting step is conducted for any suitable time period or for any time period disclosed herein, e.g., from 15 sec to 48 hr, from 1 min to 6 hr, from 1 min to 15 min, or from 1 hr to 8 hr.

Aspect 87. A supported chromium complex (or a catalyst composition comprising a supported chromium complex) having formula (A):

wherein:

each X independently is Si, Ti, Al, P, B, or Zr; and

R is a $C_1$ to $C_{36}$ hydrocarbyl group (or a $C_1$ to $C_{18}$, a $C_1$ to $C_{12}$, or a $C_1$ to $C_8$ hydrocarbyl group).

Aspect 88. The complex defined in aspect 87, wherein R is a saturated or an unsaturated, linear or branched, aliphatic hydrocarbyl group.

Aspect 89. The complex defined in aspect 87, wherein R is an aromatic hydrocarbyl group.

Aspect 90. The complex defined in aspect 87, wherein R is a benzyl, tolyl, or xylyl group.

Aspect 91. The complex defined in aspect 87, wherein R is a linear, branched, or cyclic alkyl group.

Aspect 92. The complex defined in aspect 87, wherein R is a linear, branched, or cyclic alkylene group.

Aspect 93. The complex defined in aspect 87, wherein R is a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group; or R is a methyl group, an ethyl group, a propyl group, a butyl group, a pentyl group, or a hexyl group.

Aspect 94. A composition (an oxygenated oligomer composition) comprising a compound having formula (IIa) and/or formula (IIb):

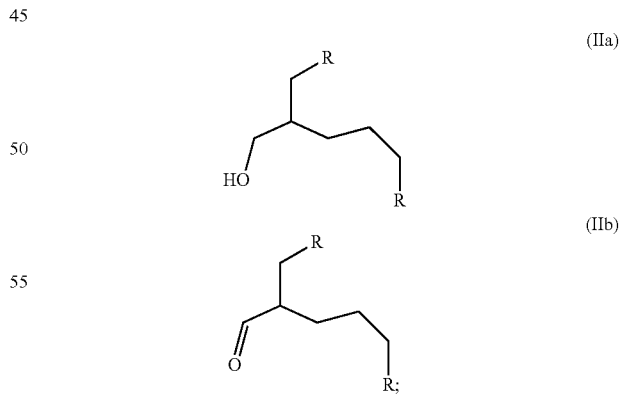

wherein R is H, a $C_6$ to $C_{18}$ aromatic group (e.g., phenyl, benzyl, etc.), or a $C_1$ to $C_{18}$ alkyl group (or a $C_1$ to $C_{12}$, a $C_1$ to $C_8$, or a $C_1$ to $C_5$ alkyl group).

Aspect 95. The composition defined in aspect 94, wherein the composition further comprises a compound having formula (IIIa) and/or formula (IIIb):

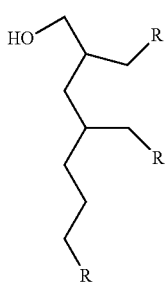

(IIIa)

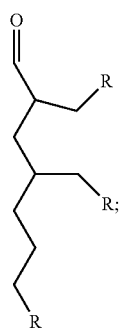

(IIIb)

wherein R is H, a $C_6$ to $C_{18}$ aromatic group (e.g., phenyl, benzyl, etc.), or a $C_1$ to $C_{18}$ alkyl group (or a $C_1$ to $C_{12}$, a $C_1$ to $C_8$, or a $C_1$ to $C_5$ alkyl group).

Aspect 96. The composition defined in aspect 94 or 95, wherein R is a linear alkyl group.

Aspect 97. The composition defined in aspect 94 or 95, wherein R is a branched alkyl group.

Aspect 98. The composition defined in aspect 94 or 95, wherein R is a hydrogen atom, a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, or an octadecyl group; or R is a methyl group, an ethyl group, a propyl group, a butyl group, a pentyl group, or a hexyl group.

Aspect 99. The composition defined in any one of aspects 94-98 produced by the process defined in any one of aspects 24 to 86, wherein the hydrocarbon reactant comprises an olefin (e.g., an α-olefin).

Aspect 100. A composition (an oxygenated oligomer composition derived from cyclohexene) comprising at least two of the following compounds: 2-cyclohexen-1,4-diol, 2-cyclohexyl cyclohexanone, 1-cyclohexyl cyclohexene, $C_{12}H_{20}O$, (1,1-bicyclohexyl)-2-one, and/or 2-cyclohexyl cyclohexanone.

Aspect 101. A composition (an oxygenated oligomer composition derived from cyclopentene) comprising at least two of the following compounds: 3-cyclopentyl cyclopentene, 2-cyclopentyl cyclopentanone, and/or 2-cyclopentylidene cyclopentanone.

Aspect 102. A supported chromium complex (or a catalyst composition comprising a supported chromium complex) having the formula (B):

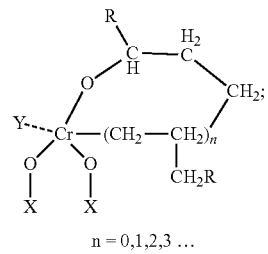

$n = 0,1,2,3 \ldots$ wherein:

each X independently is Si, Ti, Al, P, B, or Zr;

Y is nothing, $H_2O$, a $C_1$ to $C_{36}$ alcohol group (or a $C_1$ to $C_{18}$, a $C_1$ to $C_{12}$, or a $C_1$ to $C_8$ alcohol group), or a $C_2$ to $C_{36}$ ketone group (or a $C_2$ to $C_{18}$, a $C_2$ to $C_{12}$, or a $C_2$ to $C_8$ ketone group);

R is H or a $C_1$ to $C_{36}$ hydrocarbyl group (or a $C_1$ to $C_{18}$, a $C_1$ to $C_{12}$, or a $C_1$ to $C_8$ hydrocarbyl group); and n is an integer from 0 to 10 (or from 0 to 6, or from 1 to 8).

Aspect 103. A supported chromium complex (or a catalyst composition comprising a supported chromium complex) having formula (C):

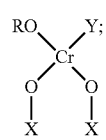

wherein:

each X independently is Si, Ti, Al, P, B, or Zr;

Y is a —OR, —R, a $C_1$ to $C_{36}$ alcohol group (or a $C_1$ to $C_{18}$, a $C_1$ to $C_{12}$, or a $C_1$ to $C_8$ alcohol group), or a $C_2$ to $C_{36}$ ketone group (or a $C_2$ to $C_{18}$, a $C_2$ to $C_{12}$, or a $C_2$ to $C_8$ ketone group); and R is a $C_1$ to $C_{36}$ hydrocarbyl group (or a $C_1$ to $C_{18}$, a $C_1$ to $C_{12}$, or a $C_1$ to $C_8$ hydrocarbyl group).

Aspect 104. A supported chromium complex (or a catalyst composition comprising a supported chromium complex) having formula (D):

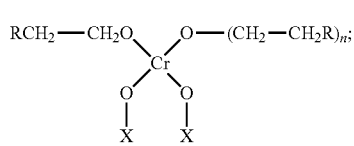

wherein:

each X independently is Si, Ti, Al, P, B, or Zr;

R is H or a $C_1$ to $C_{36}$ hydrocarbyl group (or a $C_1$ to $C_{18}$, a $C_1$ to $C_{12}$, or a $C_1$ to $C_8$ hydrocarbyl group); and n is an integer from 0 to 10 (or from 0 to 6, or from 1 to 8).

We claim:

1. A process for converting a hydrocarbon reactant into an alcohol compound and/or a carbonyl compound, the process comprising:

(i) irradiating, in an oxidizing atmosphere, the hydrocarbon reactant and a supported chromium catalyst comprising chromium in a hexavalent oxidation state with a light beam at a wavelength in the UV-visible spectrum to reduce at least a portion of the supported chromium catalyst to form a reduced chromium catalyst, or (i) contacting, in an oxidizing atmosphere, the hydrocarbon reactant comprising an olefin and a supported chromium catalyst comprising chromium in a hexavalent oxidation state to reduce at least a portion of the supported chromium catalyst to form a reduced chromium catalyst; and (ii) hydrolyzing the reduced chromium catalyst to form a reaction product comprising the alcohol compound and/or the carbonyl compound.

2. The process of claim 1, wherein;
the light beam is from a blue light source or a UV light source;
the light beam comprises wavelengths above 350 nm and below 500 nm;
the hydrocarbon reactant and the supported chromium catalyst are irradiated with an illuminance of at least 10,000 lux; or
any combination thereof.

3. The process of claim 1, wherein:
the supported chromium catalyst comprises a solid oxide, a chemically-treated solid oxide, a zeolite, or a combination thereof;
the supported chromium catalyst has a pore volume from 0.1 to 5 mL/g and a BET surface area from 50 to 2000 m$^2$/g; and
step (i) is conducted at a temperature from −100° C. to 100° C.

4. The process of claim 1, wherein the reaction product comprises an allylic alcohol.

5. The process of claim 1, wherein the supported chromium catalyst contains from 0.01 to 50 wt. % chromium, based on the weight of the supported chromium catalyst.

6. The process of claim 1, wherein:
the oxidizing atmosphere comprises air; and
a molar ratio of elemental oxygen in the oxidizing atmosphere to chromium of the supported chromium catalyst is at least 10:1.

7. The process of claim 1, wherein a molar yield of the alcohol compound and/or the carbonyl compound is from 0.1 to 5 moles of the alcohol compound and/or the carbonyl compound per mole of chromium (VI) of the supported chromium catalyst.

8. A process for converting a hydrocarbon reactant into an alcohol compound and/or a carbonyl compound, the process comprising:
(I) irradiating the hydrocarbon reactant and a supported chromium catalyst comprising chromium in a hexavalent oxidation state with a light beam at a wavelength in the UV-visible spectrum to reduce at least a portion of the supported chromium catalyst to form a reduced chromium catalyst, or
(I) contacting the hydrocarbon reactant comprising an olefin and a supported chromium catalyst comprising chromium in a hexavalent oxidation state to reduce at least a portion of the supported chromium catalyst to form a reduced chromium catalyst;
(II) subjecting the reduced chromium catalyst to an oxidizing atmosphere; and
(III) hydrolyzing the reduced chromium catalyst to form a reaction product comprising the alcohol compound and/or the carbonyl compound.

9. A process for converting a hydrocarbon reactant into an alcohol compound and/or a carbonyl compound, the process comprising:
(a) contacting the hydrocarbon reactant and a supported chromium (II) catalyst to form a treated chromium catalyst;
(b) subjecting the treated chromium catalyst to an oxidizing atmosphere; and
(c) hydrolyzing the treated chromium catalyst to form a reaction product comprising the alcohol compound and/or the carbonyl compound.

10. The process of claim 9, wherein the hydrocarbon reactant comprises a $C_1$ to $C_6$ alkane compound.

11. The process of claim 9, wherein the hydrocarbon reactant comprises an aromatic compound, a $C_2$ to $C_{12}$ olefin compound, or any combination thereof.

12. The process of claim 9, wherein the reaction product comprises an allylic alcohol.

13. The process of claim 9, wherein:
the supported chromium (II) catalyst comprises a solid oxide, a chemically-treated solid oxide, a zeolite, or a combination thereof;
the supported chromium (II) catalyst has a pore volume from 0.1 to 5 mL/g and a BET surface area from 50 to 2000 m$^2$/g; and
step (a) and step (b) are conducted, independently, at a temperature from −100° C. to 100° C.

14. The process of claim 9, wherein the supported chromium (II) catalyst contains from 0.01 to 50 wt. % chromium, based on the weight of the supported chromium (II) catalyst.

15. The process of claim 9, wherein:
the oxidizing atmosphere comprises air;
a molar ratio of elemental oxygen in the oxidizing atmosphere to chromium of the supported chromium (II) catalyst is at least 10:1; and
a molar yield of the alcohol compound and/or the carbonyl compound is from 0.1 to 5 moles of the alcohol compound and/or the carbonyl compound per mole of chromium (II) of the supported chromium (II) catalyst.

16. The process of claim 8, wherein
the light beam is from a blue light source or a UV light source;
the light beam comprises wavelengths above 350 nm and below 500 nm;
the hydrocarbon reactant and the supported chromium catalyst are irradiated with an illuminance of at least 10,000 lux; or
any combination thereof.

17. The process of claim 8, wherein:
the supported chromium catalyst comprises a solid oxide, a chemically-treated solid oxide, a zeolite, or a combination thereof;
the supported chromium catalyst has a pore volume from 0.1 to 5 mL/g and a BET surface area from 50 to 2000 m$^2$/g; and
step (I) is conducted at a temperature from −100° C. to 100° C.

18. The process of claim 8, wherein the reaction product comprises an allylic alcohol.

19. The process of claim 8, wherein the supported chromium catalyst contains from 0.01 to 50 wt. % chromium, based on the weight of the supported chromium catalyst.

20. The process of claim 8, wherein:
the oxidizing atmosphere comprises air; and
a molar ratio of elemental oxygen in the oxidizing atmosphere to chromium of the supported chromium catalyst is at least 10:1.

* * * * *